(12) United States Patent
Hidaka

(10) Patent No.: US 7,659,397 B2
(45) Date of Patent: Feb. 9, 2010

(54) PYRITHIONE COMPLEX COMPOUND, PROCESS FOR PRODUCING THE SAME AND USE THEREOF

(75) Inventor: Yasuhiro Hidaka, Sakai (JP)

(73) Assignee: YHS Ltd., Osaka (JP)

( * ) Notice: Subject to any disclaimer, the term of this patent is extended or adjusted under 35 U.S.C. 154(b) by 539 days.

(21) Appl. No.: 10/566,501

(22) PCT Filed: Oct. 22, 2004

(86) PCT No.: PCT/JP2004/015710

§ 371 (c)(1),
(2), (4) Date: Jan. 31, 2006

(87) PCT Pub. No.: WO2005/040122

PCT Pub. Date: May 6, 2005

(65) Prior Publication Data

US 2006/0246097 A1    Nov. 2, 2006

(30) Foreign Application Priority Data

Oct. 24, 2003  (JP) .............................. 2003-364295

(51) Int. Cl.
*C07F 3/06* (2006.01)
*C23F 11/00* (2006.01)
*C09K 15/26* (2006.01)

(52) U.S. Cl. ................. 546/6; 252/389.52; 252/400.52; 106/18.27; 106/18.36; 546/2

(58) Field of Classification Search ...................... 546/6, 546/2; 252/389.52, 400.52; 106/18.27, 18.36
See application file for complete search history.

(56) References Cited

U.S. PATENT DOCUMENTS 4,001,240 A    1/1977   Masaki et al.

FOREIGN PATENT DOCUMENTS

JP     53-118518     10/1978

*Primary Examiner*—Charanjit S Aulakh
(74) *Attorney, Agent, or Firm*—Wenderoth, Lind & Ponack, L.L.P.

(57) ABSTRACT

Zinc pyrithione and copper pyrithione are highly evaluated in the market as an antidandruff agent for shampoo, or an antifouling agent for ship bottom paint and fish-farming net, or an antibacterial/antifungal agent or preservative/mildewcide for industrial products and household articles. For enhancing the market value thereof, there has been a demand for a product that not only attains an increase in conventional antibacterial/antifungal effects but also exhibits novel bioactive effects and that achieves improvement with respect to problems and drawbacks relating to properties, such as solubility in seawater, and stability, such as thermal stability and weather resistance, of polymer materials. There is provided a novel pyrithione complex compound obtained by converting the conventional pyrithione metal salt to a complex compound with an oxide or hydroxide of metal such as zinc, copper or aluminum. As compared with the conventional pyrithione metal salt, this complex compound exhibits superior antibacterial/antifungal effects, newly realizes a hair-regrowing effect and successfully attains improvement with respect to the solubility in seawater and thermal stability/weather resistance of polymer materials.

14 Claims, 11 Drawing Sheets

[Fig. 1]
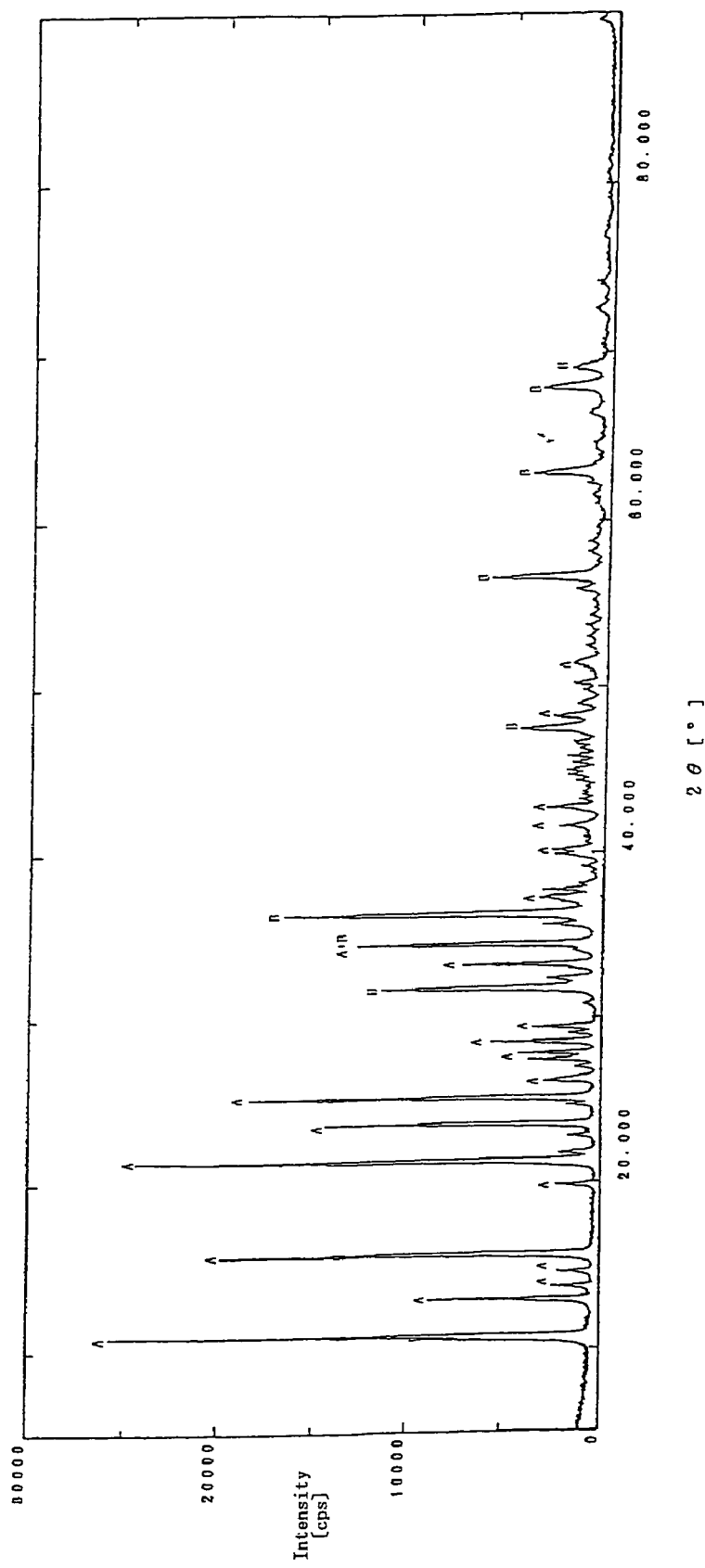

[Fig. 2]
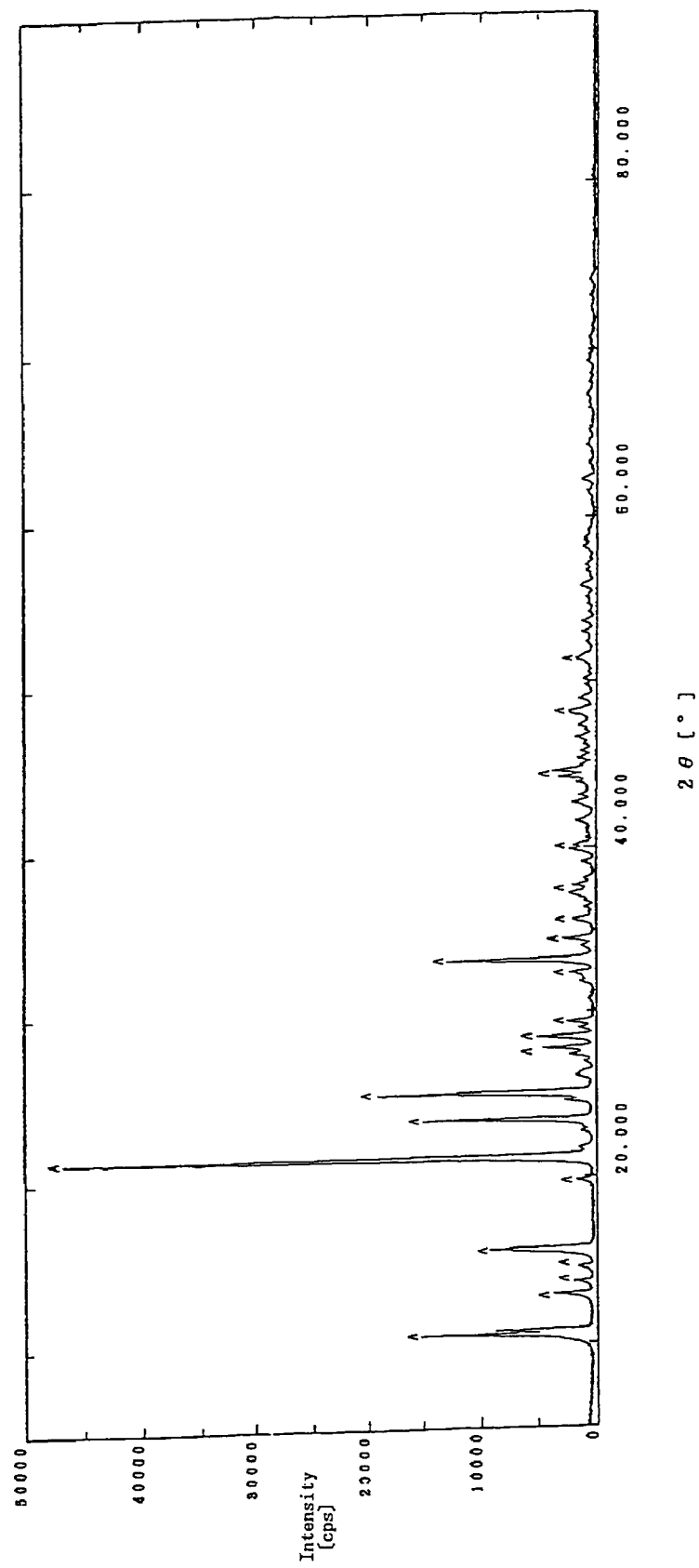

[Fig. 3]
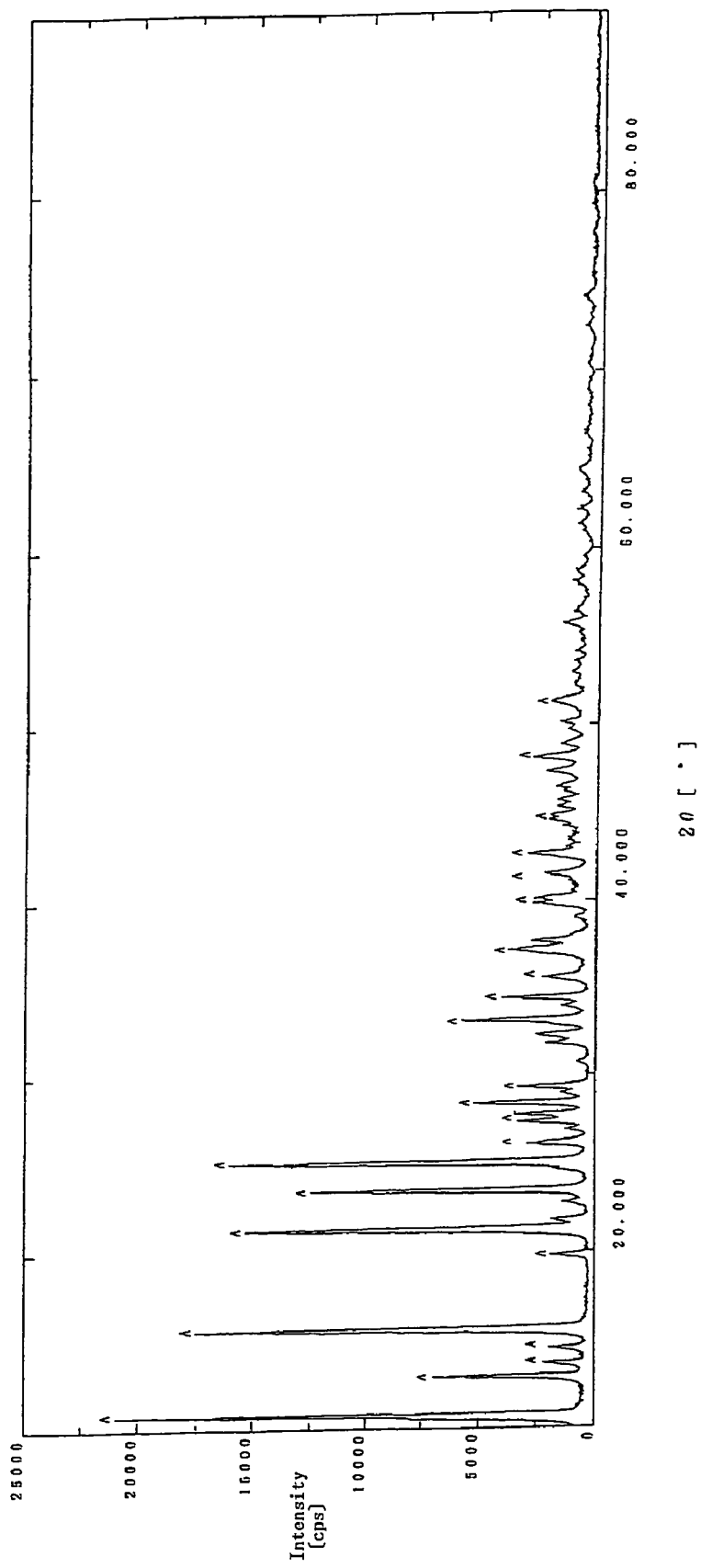

[Fig. 4]
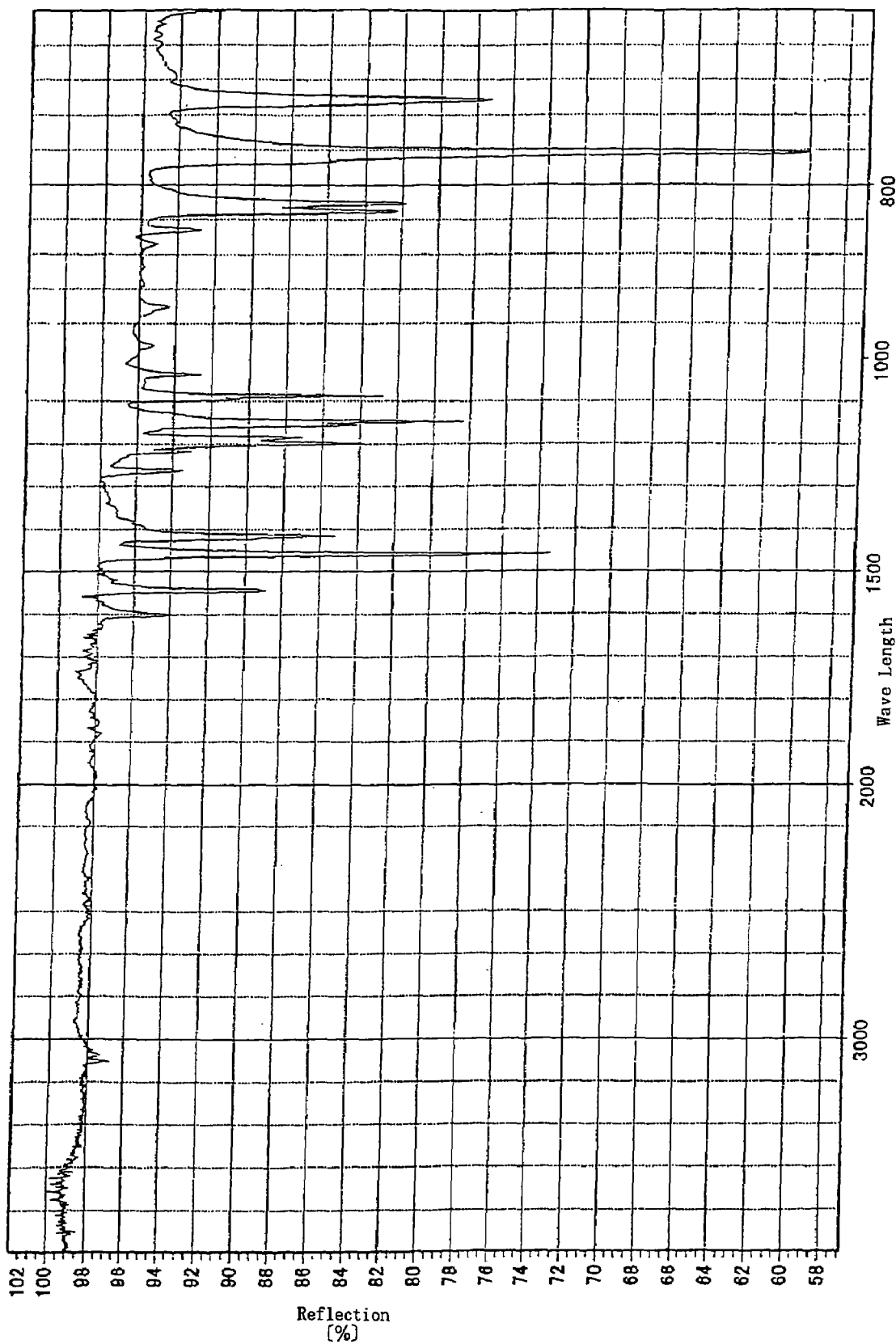

[Fig. 5]
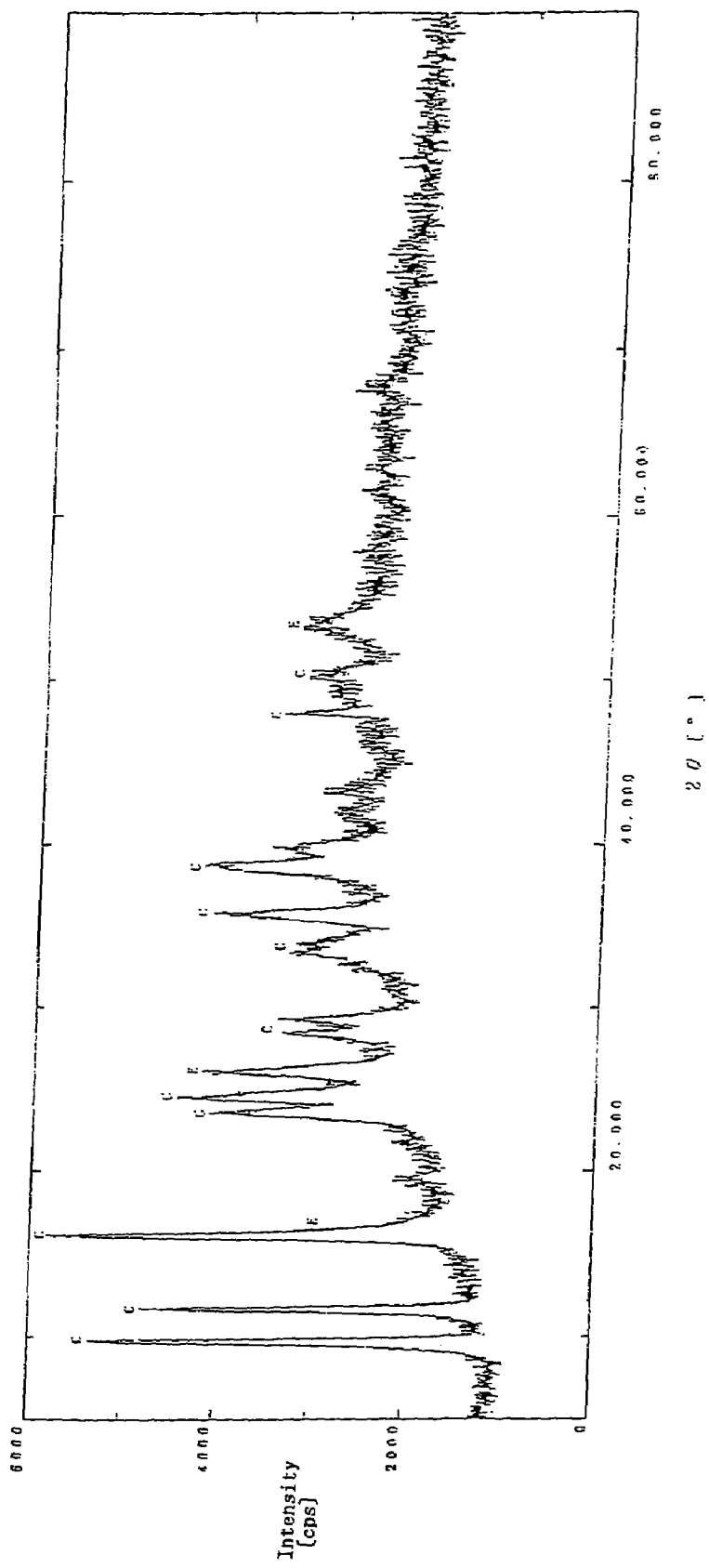

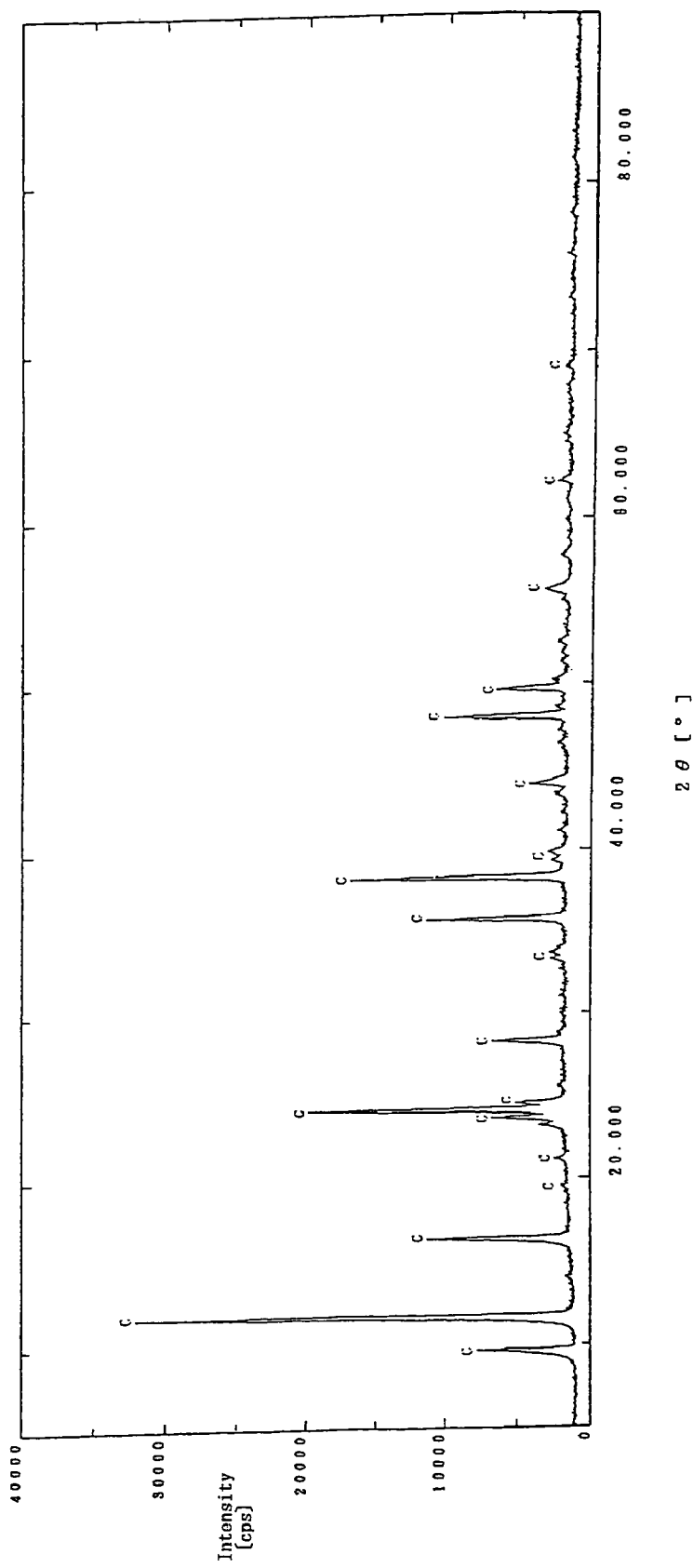
[Fig. 6]

[Fig. 7]
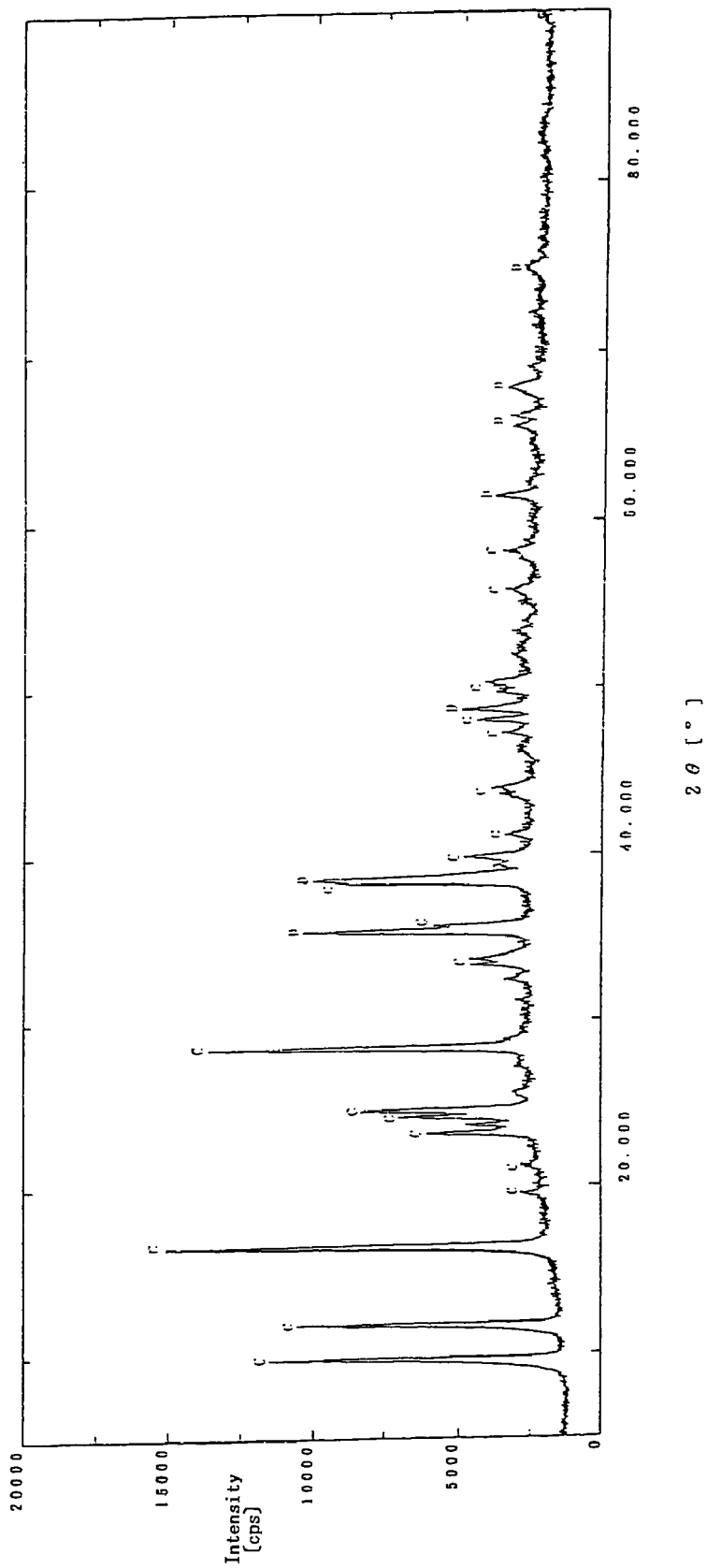

[Fig. 8]
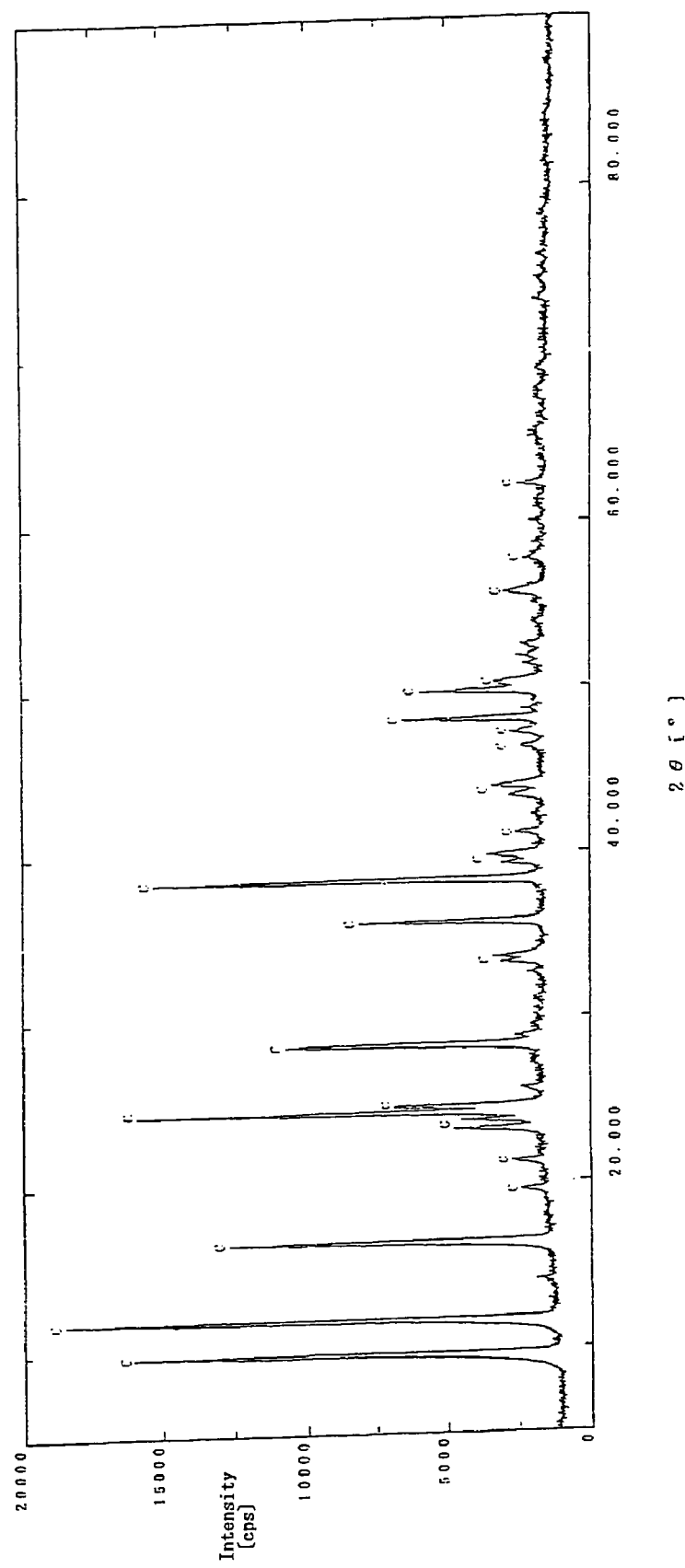

[Fig. 9]
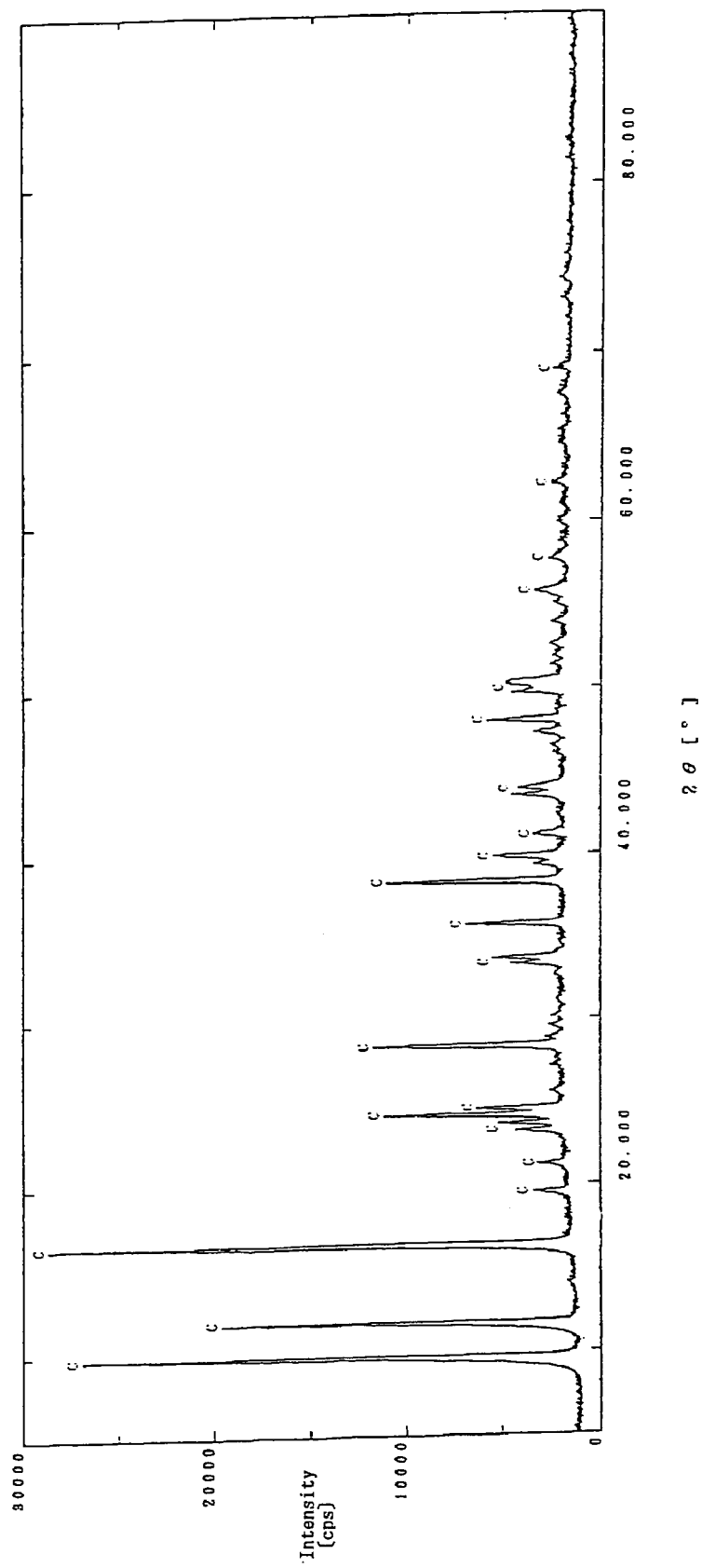

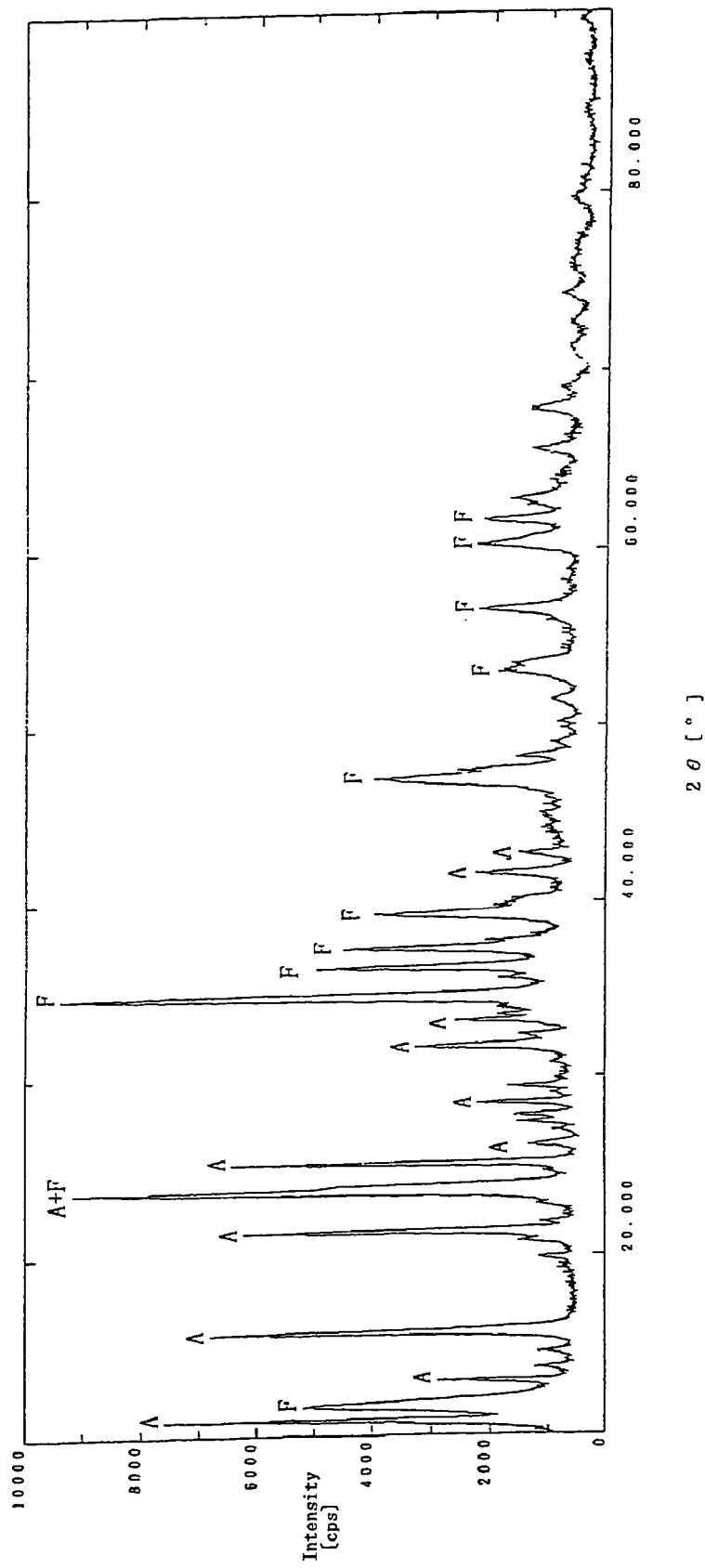
[Fig. 10]

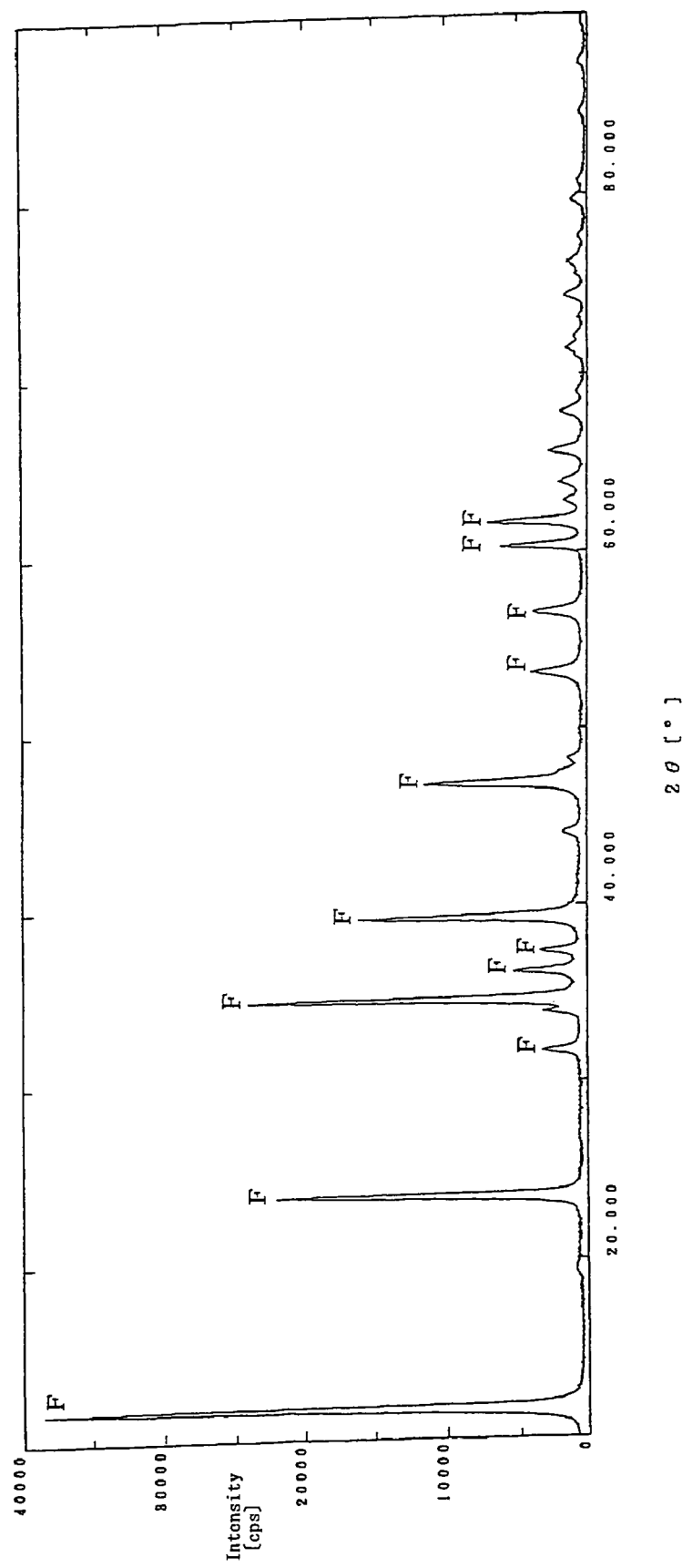
[Fig. 11]

PYRITHIONE COMPLEX COMPOUND, PROCESS FOR PRODUCING THE SAME AND USE THEREOF

This application is a U.S. national stage of International Application No. PCT/JP2004/015710 filed Oct. 22, 2004.

TECHNICAL FIELD

The present invention relates to a novel complex compound of inorganic/organic compounds comprising an inorganic metal compound and a pyrithione metal salt, to a process for producing the complex compound and to a use of the complex compound. The present invention relates, particularly, to a complex compound comprising an oxide or hydroxide of a metal such as zinc, copper or aluminum and a pyrithione metal salt with high content, to a process for producing the complex and to a use of the complex. The complex compound of the present invention relates to a novel pyrithione complex compound which are superior in each effect and has various properties superior to zinc pyrithione formulated currently in hair-care products such as shampoos and hair rinses, zinc pyrithione or copper pyrithione as an underwater antifouling agent formulated in ship bottom paints and antifouling agent for fish-farming nets, zinc pyrithione as an antibacterial/antifungal agent to be added to polymer materials such as plastic products, rubber products and fiber products or as a preservative/mildewcide for aqueous products and household articles such as industrial water, emulsions, water suspension products and wood treating agents and zinc pyrithione as an antibacterial/deodorant agent formulated in foot powders.

BACKGROUND ART

The technology used to add a pyrithione metal salt to a part of a metal oxide or metal hydroxide is known. For example, there are descriptions as to technologies for forming metal pyrithione as a shell on the surface of a metal oxide or metal hydroxide used as a core and as to a biocidal composite in the publication of Japanese Patent Publication (Laid-Open) No. 2002-521339. However, in these technologies, the amount of the metal pyrithione to be added to a metal oxide or metal hydroxide is merely about 10 W % based on the metal oxide or metal hydroxide and the biological activity of the pyrithione metal salt is therefore insufficiently made effective.

Also, technologies for enhancing the efficiency of metal pyrithione by using the metal pyrithione and a metal oxide or metal hydroxide are known. For example, the publication of Japanese Patent Publication (Laid-Open) No. 2003-522734 suggests that the use of a combination of zinc oxide, copper oxide, zinc hydroxide or copper hydroxide and metal pyrithione increases antibacterial and antifungal efficacy. However, the effect of this combination is not developed as long as the metal oxide or the metal hydroxide does not generate a metal ion and therefore the use of this combination is limited to aqueous products and also, a stable effect is not obtained.

Also, in the publication of Japanese Patent Publication Laid-Open (JP-A) No. 51-95078, a method in which pyridinethiol is reacted with a zinc salt in the presence of a base and water is disclosed as a method of producing a 2-pyridylthio zinc oxy complex. The method of producing this complex is similar to a method of producing a pyrithione complex compound which is a compound obtained when M is zinc, Q is one oxygen atom, D is zinc pyrithione, y=0, p+2q=0, n=0, neither A nor B are present and x is ⅓ among the compounds represented by the formula (I) which will be explained later. However, the both methods differ from each other as to the product to be produced and its effect in the point that first, the materials obtained in both methods are different from each other and second, the zinc pyrithione/zinc oxide complex compound of the present invention has biocidal activity whereas the above 2-pyridylthio zinc oxy complex shows the effect of preventing a deterioration of a resin which is caused by the contact with a heavy metal.

Patent Reference 1: Japanese Patent Publication (Laid-Open) No. 2002-521339.

Patent Reference 2: Japanese Patent Publication (Laid-Open) No. 2003-522734.

Patent Reference 3: Japanese Patent Publication (Laid-Open) No. S51-95078.

DISCLOSURE OF INVENTION

Zinc or copper pyrithione which has been put to practical use is a compound which has the structural formula shown below and is highly estimated for the performance of the compound in each application, but unnecessarily poses no problem concerning efficiency, effect, physicochemical properties, stability and the like.

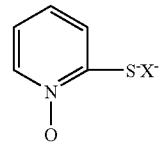

In the formula, X represents a metal of 1/2Zn 1/2Cu.

As to zinc pyrithione to be used as an antidandruff agent for hair-care products such as shampoos and hair rinses, more than 40 years have passed since this zinc pyrithione was put to the market. However, this zinc pyrithione has been desired to impart a stronger and more stable effect.

zinc pyrithione and copper pyrithione as an underwater antifouling agent formulated in ship bottom paints and fish-farming net antifouling agents have problems as to solubility in seawater. Organotin containing antifouling agents that have not been used because of environmental toxicity problem are bound with an acrylic resin as a binder and is the so-called self-polishing type resin that is integrated with the resin and eluted into seawater by hydrolysis. This antifouling agent develops its effect very efficiently. However, a pyrithione type antifouling agent is not combined with a resin and therefore has a problem as to such an eluting mechanism that it is eluted more rapidly than the resin, or is insufficiently dissolved in seawater even if it is eluted together with the resin because of a difference in solubility between the pyrithione type antifouling agent and the self-polishing type resins. Specifically, the solubility of zinc pyrithione in seawater is too high whereas the solubility of copper pyrithione in seawater is too low. Zinc pyrithione used as an antibacterial and antifungal agent for polymer materials has a more unsatisfactory effect than other antibacterial and antifungal agents and also has problems concerning heat stability during processing and the durability of the product. Zinc pyrithione used as a preservative for emulsion paints, adhesives, coating colors, polymer emulsions and industrial water has an unsatisfactory effect on, particularly, bacteria belonging to the genus Pseudomonas. Also, zinc pyrithione used as foot powders is unnecessarily has a sufficient antibacterial/deodorant effect.

The inventors of the present invention have made earnest studies to solve the above problem and, as a result, surprisingly found that a pyrithione complex compound represented by the following formula (I) solves all the above problems that conventional zinc or copper pyrithione has. The pyrithione complex compound of the present invention is fundamentally different from that obtained by conventional technologies in the point that it is not an adduct on the surface of metal oxide or a metal hydroxide but is a uniform complex compound having a certain chemical structure.

Accordingly, the present invention relates to:

(1) a pyrithione complex compound represented by the formula (I):

$$xMQ \cdot yM'Q' \cdot D \cdot [A_p \cdot B_q] \cdot nH_2O \quad (I)$$

wherein, M represents a divalent metal, M' represents a trivalent metal, Q represents one oxygen atom or two hydroxyl groups, Q' represents 3/2 oxygen atoms or 3 hydroxyl groups, x, y, p, q and n respectively denote 0 or a positive number satisfying the following equations: $0 \leq x \leq 7$, $0 \leq y \leq 6$, $0 \leq p+2q \leq 6/5$ and $0 \leq n \leq 7$, (provided that x and y are not 0 at the same time), D represents $M(Py)_{2-p-2q}$ when $x \neq 0$ and $M'(Py)_{3-3p/2-3q}$ when $x=0$, Py represents 2-pyridylthio-N-oxide, A represents a monovalent anion other than Py or shows that it does not exist and B represents a divalent anion or shows that it does not exist;

(2) a pyrithione complex compound according to the above (1), wherein, in the formula (I), M is at least one divalent metal selected from Zn and Cu, M' is Al, A is a monovalent anion selected from Cl and $NO_3$ or shows that it does not exist, B is at least one divalent anion selected from $CO_3$ and $SO_4$ or shows that it does not exist and x, y, p, q, n, Q, Q' and D respectively have the same meaning as above;

(3) a pyrithione complex compound according to the above (1), wherein, in the formula (I), M is zinc, Q is one oxygen atom, D is zinc pyrithione, y=0, p+2q=0, n=0, A and B do not exist and x is ⅓;

(4) a pyrithione complex compound according to the above (1), wherein, in the formula (I), M is copper, Q is one oxygen atom or two hydroxyl groups, D is copper pyrithione, y=0, p+2q=0, $0 \leq n \leq 1$, A and B do not exist and x is ⅓.

(5) a process for producing a pyrithione complex compound represented by the formula (I):

$$xMQ \cdot yM'Q' \cdot D \cdot [A_p \cdot B_q] \cdot nH_2O \quad (I)$$

wherein, M represents a divalent metal, M' represents a trivalent metal, Q represents one oxygen atom or two hydroxyl groups, Q' represents 3/2 oxygen atoms or 3 hydroxyl groups, x, y, p, q and n respectively denote 0 or a positive number satisfying the following equations: $0 \leq x \leq 1$, $0 \leq y \leq 1$, $0 \leq p+2q < 6/5$ and $0 \leq n \leq 2$, (provided that x and y are not 0 at the same time), D represents $M(Py)_{2-p-2q}$ when $x \neq 0$ and $y=0$ and $M'(Py)_{3-3p/2-3q}$ when $x=0$ and $y \neq 0$ where Py represents 2-pyridylthio-N-oxide and A and B do not exist and either x or y is 0, which comprises adding ½ to 2 equivalent mol of an aqueous solution of a divalent or trivalent water-soluble metal salt and ¾ to 3 equivalent mol of an aqueous alkali hydroxide solution to an aqueous alkali pyrithione solution and reacting the mixture at a pH of 9 to 12 to collect the precipitates wherein;

(6) a process for producing a pyrithione complex compound represented by the formula (I):

$$xMQ \cdot yM'Q' \cdot D \cdot [A_p \cdot B_q] \cdot nH_2O \quad (I)$$

wherein, M represents a divalent metal, M' represents a trivalent metal, Q represents one oxygen atom or two hydroxyl groups, Q' represents 3/2 oxygen atoms or 3 hydroxyl groups, x, y, p, q and n respectively denote 0 or a positive number satisfying the following equations: $0 \leq x \leq 7$, $0 \leq y \leq 6$, $0 \leq p+2q \leq 6/5$ and $0 \leq n \leq 7$, (provided that x and y are not 0 at the same time) D represents $M(Py)_{2-p-2q}$ where Py represents 2-pyridylthio-N-oxide, A represents a monovalent anion other than Py or shows that it does not exist, B represents a divalent anion or shows that it does not exist and $x \neq 0$ and $y \neq 0$, which comprises adding a water soluble salt of a divalent metal and a water-soluble salt of a trivalent metal to an aqueous solution containing an alkali pyrithione, an alkali hydroxide and, if necessary, a monovalent anion other than pyrithione and/or a divalent anion, adjusting the mixture to a pH 8 to 10 and collecting the obtained precipitates, (7) a process for producing a pyrithione complex compound according to the above (6), wherein, in the formula (I), M is Zn, M' is Al, A is at least one monovalent anion selected from Cl and $NO_3$ or shows that it does not exist, B is at least one divalent anion selected from $CO_3$ and $SO_4$ or shows that it does not exist and x, y, p, q, n, Q, Q' and D respectively have the same meaning as above;

(8) a process for producing a pyrithione complex compound according to the above (5), wherein, in the formula (I), M is zinc, Q is one oxygen atom, D is zinc pyrithione, y=0, p+2q=0, n=0, A and B do not exist and x is ⅓;

(9) a process for producing a pyrithione complex compound according to any one of the above (5) and (8), wherein the pyrithione complex compound contains zinc oxide or a mixture of zinc oxide and zinc pyrithione as a byproduct and the exothermic peak temperature in thermal analysis (DTA) is 322 to 335° C.;

(10) a process for producing a pyrithione complex compound according to the above (5), wherein, in the formula (I), M is copper, Q is one oxygen atom or two hydroxyl groups, D is copper pyrithione, y=0, p+2q=0, $0 \leq n \leq 1$, A and B do not exist and x is ⅓;

(11) a process for producing a pyrithione complex compound according to any one of the above (5) and (10), wherein the pyrithione complex compound contains copper (II) oxide or a mixture of copper oxide (II) and copper pyrithione as a byproduct and the exothermic peak temperature in thermal analysis (DTA) is 282 to 294° C.;

(12) an antidandruff agent comprising one or more of the pyrithione complex compounds according to any one of the above (1) to (4);

(13) A hair-care product comprising the antidandruff agent according to the above (12) or the antidandruff agent and zinc oxide;

(14) an underwater antifouling agent comprising one or more of the pyrithione complex compounds according to any one of the above (1) to (4);

(15) an underwater antifouling agent comprising one or more of the pyrithione complex compounds according to any one of the above (1) to (4), a binder and an inorganic copper compound and/or inorganic zinc compound as effective components;

(16) an underwater antifouling agent according to the above (15), wherein the binder is an acrylic resin, the inorganic copper compound is at least one type selected from copper (I) oxide, copper (II) oxide and copper thiocyanate and the inorganic zinc compound is zinc oxide;

(17) a preservative/mildewcide or an antibacterial/antifungal agent comprising one or more of the pyrithione complex compounds according to any one of the above (1) to (4) as effective components; and

(18) An aqueous product comprising the pyrithione complex compound according to the above (3) or a mixture of the pyrithione compound and zinc oxide and a 2-isothiazolone type preservative.

In the pyrithione complex compound represented by the above formula (I) according to the present invention, examples of the divalent metal represented by M include Zn, Mg, Ca, Ba, Cu and Fe and examples of the trivalent metal represented by M' include Al and Fe. Although any material may be used as the water soluble salts of these metals, a nitrate, sulfate, hydrochloride or the like is preferably used.

Preferable examples of the alkali pyrithione include a sodium salt or potassium salt of pyrithione, a sodium salt being more preferable.

Examples of the monovalent anion represented by A other than Py include monovalent inorganic anions such as $NO_3^-$ and $Cl^-$ and monobasic organic acids, e.g., acetic acid, propionic acid, benzoic acid and benzenesulfonic acid. Examples of the divalent anion represented by B include inorganic anions such as $CO_2^{2-}$, $SO_4^{2-}$, $HPO_4^{2-}$ and $HPO_3^{2-}$ and dibasic organic acids such as succinic acid, phthalic acid, salicylic acid and maleic acid.

In the formula (I), x, y, p, q and n respectively denote 0 or a positive satisfying the following equations: $0 \leq x \leq 7$, $0 \leq y \leq 6$, $0 \leq p+2q \leq 6/5$ and $0 \leq n \leq 7$ number (provided that x and y are not 0 at the same time) and more preferably the following equations: $0 \leq x \leq 1$, $0 \leq y \leq 1$, $0 \leq p+2q \leq 2/5$ and $0 \leq n \leq 2$ when $x \neq 0$ and $y=0$ or $x=0$ and $y \neq 0$ and the following equations: $0 \leq x \leq 5$, $0 \leq y \leq 3$, $0 \leq p+2q \leq 2/5$ and $0 \leq n \leq 4$ when $x \neq 0$ and $y \neq 0$ (provided that x and y are not 0 at the same time).

The pyrithione compound represented by the formula (I) in which $x \neq 0$ and $y=0$ or $x=0$ and $y \neq 0$ may be obtained in the following manner: a water-soluble salt of a divalent metal represented by M or a water-soluble salt of a trivalent metal represented by M' is added to an aqueous mixed solution prepared by adding an alkali hydroxide, for example, sodium hydroxide, potassium hydroxide and ammonium and preferably sodium hydroxide to a pyrithione alkali metal salt, for example, a sodium salt or potassium salt and preferably a sodium salt, the mixture is reacted at a pH of 9.0 to 12.0 and preferably 9.5 to 11.5 and then, as required, the resulting mixture is adjusted to pH 7 to 10 and preferably 8 to 10, followed by aging the mixture at 0 to 80° C. and preferably 10 to 60° C. for 1 to 10 hours and preferably 3 to 5 hours.

As to the ratio of each raw material to be used, it is only required that the alkali hydroxide be formulated in an amount of ¾ to 3 equivalent mol and preferably 1 to 2 equivalent mol and the aqueous salt of a divalent or trivalent metal ½ to 2 equivalent mol and preferably 1 to 3/2 equivalent mol based on the alkali metal salt of pyrithione. Also, each raw material is preferably used as an aqueous solution having a concentration of 0.01 to 10 mol and preferably 0.02 to 5 mol. When these raw materials are used and reacted, it is necessary that the pH in the reaction be 9.0 to 12.0. When, for example, each molar ratio of zinc sulfate and sodium hydroxide to sodium pyrithione is 2, the pH of the reaction solution is 7 and therefore no pyrithione complex compound is produced though the aging process is performed at pH of 9.5. Also, when the pH is 12.0 or more in the reaction, the yield of the pyrithione complex compound is greatly reduced.

The pyrithione compound represented by the formula (I) in which $x \neq 0$ and $y \neq 0$ may be obtained in the following manner: an aqueous mixed solution of a water-soluble salt of a divalent metal represented by M or a water-soluble salt of a trivalent metal represented by M' is added to an aqueous mixed solution of a pyrithione alkali metal salt, for example, a sodium salt or potassium salt, an alkali hydroxide, for example, sodium hydroxide, potassium hydroxide and ammonium and preferably sodium hydroxide and as required, an alkali metal salt, for example, a sodium salt or potassium salt of a monovalent or divalent anion represented by A or B, the mixture is adjusted to pH 7 to 11 and preferably 8 to 10 and reacted at 0 to 60° C. and preferably 10 to 30° C. for 1 to 6 hours and preferably 1 to 3 hours to obtain the target pyrithione complex compound as precipitates.

These precipitates obtained by the reaction, though it may be collected by filtration, is preferably treated as it is at 90 to 120° C. for 7 to 25 hours in hot water for 7 to 25 hours or washed with water after collected by filtration to make a wet cake, which is then transferred to underwater, washed with water according to the need, then treated at 90 to 120° C. for 7 to 25 hours in hot water and then collected. The precipitates obtained in this manner are dried at 50 to 60° C. for about 5 hours, followed by pulverizing to form a white powder.

If the pyrithione alkali metal salt is mixed with the water-soluble salt of a divalent metal represented by M and the water-soluble salt of a trivalent metal represented by M' from the first, a metal pyrithione is produced and the target pyrithione complex compound is obtained only insufficiently.

The ratio of each raw material to be used, each raw material may be used in the ratio corresponding to the percentage composition of the target pyrithione complex compound. Also, each raw material may be mixed as an aqueous solution containing each raw material in a concentration of 0.01 to 10 mol and preferably 0.02 to 5 mol.

The pyrithione complex compound represented by the formula (I) in the present invention is those in which 40 W % or more and preferably 80 W % or more of the anions excluding Q or Q' is substituted with pyrithione.

The pyrithione complex compound represented by the formula (I) is used as an antidandruff agent to be formulated in hair-care products such as shampoos and hair rinses like conventional zinc pyrithione. The growth inhibitive effect (MIC) on Malassezia furfur which was an index of dandruff preventive effect was the same as that of zinc pyrithione. Also, the primary irritation (criterion by the Draize method) to the oculus membrane mucosa of an albino rabbit showed the same result (slightly irritant) as that of zinc pyrithione when instilling as an aqueous 2.0 W % suspension in the eye. However, the zinc pyrithione/zinc oxide complex compound of the present invention has the possibility of being a new type of hair-care product which has not only higher antibacterial ability to *Staphylococcus aureus* and *Escherichia coli* which are skin inhabitants than zinc pyrithione, but also an antidandruff effect and hair growth effect at the same time. U.S. Pat. No. 6,033,653 suggests that zinc oxide has a hair growth effect and is formulated as a hair regrowth agent in an amount of 1.25 to 1.56 W % in a shampoo. However, it is more effective to apply zinc oxide in the form of a zinc pyrithione/zinc oxide complex compound which has higher affinity to the head skin than in the form of an inorganic compound zinc oxide. Also, the zinc pyrithione/zinc oxide complex compound and zinc pyrithione were respectively added to purified water in an amount of 2% by weight and each suspension was allowed to stand in a well-lighted room to observe the degree of coloration of the suspension. As a result, the supernatant obtained by adding zinc pyrithione was colored in yellow after one week whereas the liquid obtained by adding the complex compound of the present invention was colored to such an extent that it was slightly yellowed. This clearly shows that a shampoo prepared by formulating the complex compound of the present invention is more stable to light.

The complex compound of the present invention is formulated in a concentration of 0.5 to 5 W % and preferably 1 to 3 W % in a liquid shampoo, in a concentration once or twice the above concentration in a creamy shampoo, and in a concentration of 0.1 to 1 W % and preferably 0.2 to 0.6 W % in a hair rinse.

Also, as the base of a shampoo, at least one or two or more types among anionic surfactants, for example, each sodium salt, triethanolamine salt or ammonium salt of lauryl sulfate, ethoxylauryl sulfate or alkylaryl sulfonate and nonionic surfactants such as polyoxyethylene sorbitan monostearate are used, in addition to this, one or two or more types of purified water, foaming agents, perfumes, thickeners and preservative are added and also various active ingredients and/or functional components are added to give consumers' satisfaction.

The pyrithione complex compound represented by the above formula (I) is used as antifouling agents for ship bottom paints, antifouling agents for fish-farming nets and antifouling agents for underwater construction materials. This compound has more preferable solubility in seawater as compared with zinc pyrithione and copper pyrithione that are frequently used as antifouling agents for ship bottom paints in place of organic tin. For example, the pyrithione complex compound of the present invention has a solubility closer to that of a self-polishing resin in seawater. The solubility of zinc pyrithione and copper pyrithione in seawater are 6 ppm or more and 0.2 ppm or less respectively whereas the solubility of the zinc pyrithione/zinc oxide complex compound and copper pyrithione/zinc oxide complex compound in seawater are about 3 to 4 ppm and about 0.6 ppm respectively. It is therefore possible to improve the conventional problem as to too rapid elution of zinc pyrithione and inferior dissolution of copper pyrithione in a cold seawater zone.

The pyrithione complex compound of the present invention is formulated in an amount of 0.1 to 15 W % and preferably 1 to 5 W % in a ship bottom paint and in an amount of 0.1 to 10 W % and preferably 1 to 7 W % in an antifouling agent for fish-farming nets.

As a binder for ship bottom paints, for example, an acrylic resin, vinyl resin or chlorinated rubber is used. As to, particularly, an acrylic resin, a remarkable attention is focused on such a type that is dissolved gradually into seawater by hydrolysis to a water-soluble type by combining an organic silicon group or an organic acid group with a part of an acrylic acid group via zinc or copper atom to impart self-polishing function.

Metal pyrithiones used as antifouling agents are effective on algae but unnecessarily effective on animal type organisms such as a corn barnacle. For this, these metal pyrithiones are usually used in combination with one or two or more copper compounds such as cuprous oxide and copper thiocyanate. Also, in order to obtain a "preferable elution concentration/time" curve, the pyrithione complex compound of the present invention may be used in combination with zinc pyrithione or copper pyrithione that has been used so far. In order to obtain additional complementary or synergetic effects, the pyrithione complex compound of the present invention may be used in combination with one or two or more types of antifouling active components other than copper compounds such as cuprous oxide and copper thiocyanate, for example, zinc oxide, a heavy metal salt of a dithiocarbamic acid compound, thiuram disulfide compound, 4,5-dichloro-N-octyl-1,2-isothiazolin-3-one (trade name: "Sea Nine", manufactured by Rohm and Haas), triphenylborane pyridine salt and triazine type compounds "Irgarol 1051", manufactured by Ciba Specialty Chemicals Inc. A solvent such as xylene is further used as essential components other than the binder and the antifouling agent and the composition is adjusted to an appropriate PVC (pigment volume concentration) by using color pigments and extenders. Moreover, as desired, besides rosin to be added to control the elution of the above copper compound and to improve coating-function, one or more of a viscosity regulator, a dispersing agent and an antiskinning agent may be used.

When the pyrithione complex compound of the present invention is used as an antifouling agent for fish-farming nets, it may be used in combination with a binder such as an acrylic resin which is an essential component, a solvent such as xylene, at least one or more types of a copper powder, cuprous oxide, triphenylborane compound and zinc oxide effective for preventing animal type organisms from sticking and a heavy metal dithiocarbamate compound which is particularly effective for preventing a hydrozoan from sticking. Moreover, the pyrithione complex compound of the present invention may be used in combination with an elution controlling/effect promoting agent such as t-nonyl polysulfide.

The pyrithione complex compound of the present invention when it is a typical complex compound of a metal oxide and a metal pyrithione in the case where x≠0 and y=0 differs from that obtained when it is a typical complex compound of a hydrotalcite in the case where x≠0 and y≠0 in antibacterial and antifungal mechanism. Specifically, in the former case, the metal oxide and metal pyrithione penetrate into the cells of bacteria in the condition that the both are united with each other, producing an antibacterial and antifungal activity one to four times that of metal pyrithione due to the synergetic effect of the both. In the case of a mixture of a pyrithione metal salt and a metal salt in the aforementioned known art, the synergetic effect of the both is not produced if the metal oxide does not form metal ions such as zinc and copper ions. However, in the case of the complex compound of the present invention, the metal oxide penetrates into cells even if it does not take a metal ion form, so that the synergetic effect can be produced without fail. In the latter case, the pyrithione complex compound has higher durability and a pyrithione anion in the pyrithione complex compound is released by an exchange of an anion of a chlorine ion. Therefore, this complex compound is useful as an antibacterial and antifungal agent and a stabilizer for vinyl chloride resins that tend to generate free hydrogen chloride by a deterioration.

The pyrithione complex compound represented by the above formula (I) is formulated as an antibacterial and antifungal agent in an amount of 0.01 to 0.5 W % in polymer materials such as plastics, rubbers and fibers and household articles such as toilet articles and kitchen articles. The pyrithione complex compound of the present invention is formulated in aqueous products such as industrial water, emulsions and aqueous suspensions as a preservative or in place of conventional zinc pyrithione. In these objects, the pyrithione complex compound of the present invention is prepared into an aqueous 5 to 20 W % suspension additionally containing a thickener and, as required, an antifoaming agent. According to its use or object, the concentrate of the pyrithione complex compound is diluted to a concentration of 0.01 to 0.5 W % based on the active ingredient base. The industrial water includes, for example, circulating water for a cooling tower and white water for paper-making, the emulsion includes, for example, a raw material polymer emulsion, emulsion paint and adhesive and the water suspension products includes drilling water and coating colors. Also, the pyrithione complex compound of the present invention is formulated as antifungal agent for wood in an amount of 1 to 20 W % in an oily suspension such as a kerosene or in water suspension.

When the pyrithione complex compound of the present invention is used by kneading it in polymer materials such as plastic products, rubber products and fiber products, it is superior in antibacterial and antifungal efficacy to zinc pyrithione and also superior in prolonged efficacy to zinc pyrithione because it migrates to the surface of a resin, rubber or fiber more slowly than zinc pyrithione. Moreover, the pyrithione complex compound produced by the process of the present invention generally contains metal oxides such as zinc oxide as byproducts. However, these metal oxides are associated with the pyrithione complex compound and the by-produced metal pyrithione, which raises thermal decomposition temperature and therefore, the pyrithione complex compound of the present invention has superb heat stability during processing.

When the pyrithione complex compound of the present invention is added to the aforementioned aqueous products upon use, it is preferably used in combination with other industrial biocides. Generally, pyrithione compounds are biocides having broad spectrum of bacteria and fungi. However, it is relatively weak effects on bacteria belonging to the genus Pseudomonas and it is effective to use it in combination with, for example, 5-chloro-2-methyl-4-isothiazolin-3-one, formaldehyde release-type bronopol or 1,3,5-tris(2-hydroxyethyl)hexahydro-s-triazine which has a strong activity against the genus Pseudomonas. Also, 2-isothiazolone type compounds used widely as a preservative, for example, 1,2-benzisothiazolin-3-one, 5-chloro-2-methyl-4-isothiazolin-3-one and 2-methyl-4-isothiazolin-3-one are severely irritant against the skin and it is therefore required to take care for handling in formulating. However, if these 2-isothiazolone type compounds are used in combination with the pyrithione complex compound of the present invention, the irritation against the skin can be moderated.

When the pyrithione complex compound represented by the formula (I) in the present invention is used as an antibacterial and antifungal agent for foot powders, it is formulated in an amount of 0.05 to 10.0 W % and preferably 0.5 to 5 W % in a medium such as talc, kaolin or rosin, then a small amount of a perfume is added and the resulting powder is used as it is or after it is made into the form of aerosol. The pyrithione complex compound of the present invention has an excellent antibacterial and antifungal effect and therefore inhibits the growth of bacteria that causes the generation of offensive odors and also, metal oxides such as zinc oxide contained as the complex compound or byproducts react with organic acids or fatty acids such as lactic acid, butyric acid and caproic acid, which are malodorous, to produce a deodorant effect. The pyrithione complex compound of the present invention has an effect on antibacterial and deodorant activity particularly in shoes.

BRIEF DESCRIPTION OF DRAWINGS

FIG. 1 is an X-ray diffraction chart of a white powder in Example 3.

FIG. 2 is an X-ray diffraction chart of a chloroform extract in Example 3.

FIG. 3 is an X-ray diffraction chart of zinc pyrithione (reagent manufactured by Wako Pure Chemical Industries, Ltd.).

FIG. 4 is an IR chart of a white powder in Example 3.

FIG. 5 is an X-ray diffraction analysis of a dark green powder in Example 8.

FIG. 6 is an X-ray diffraction chart of a chloroform extract in Example 8.

FIG. 7 is an X-ray diffraction analysis of a dark green powder in Example 9.

FIG. 8 is an X-ray diffraction chart of a chloroform extract in Example 9.

FIG. 9 is an X-ray diffraction chart of copper pyrithione (manufactured by API Corporation).

FIG. 10 is an X-ray diffraction chart of a white powder in Example 12(ii).

FIG. 11 is an X-ray diffraction chart of carbonic acid type hydrotalcite $Zn_4Al_2(OH)_{12}(CO_3) \cdot 3H_2O$.

EXPLANATIONS OF THE SYMBOLS

A: Zinc pyrithione
B: Zinc oxide
C: Copper pyrithione
D: Copper (II) oxide
E: Copper (II) hydroxide
F: Carbonic acid-made hydrotalcite

BEST MODE FOR CARRYOUT THE INVENTION

The present invention will be explained in detail by examples.

Example 1

Synthesis of a Compound (1)

41.5 mL of an aqueous 1 mol sodium pyrithione solution and 50 mL of an aqueous 2 mol sodium hydroxide NaOH solution were combined and placed in a 300 mL conical flask, which was then kept at 20° C. 120 mL of an aqueous solution containing 12.0 g (which was mol equivalent to that of sodium pyrithione) of zinc sulfate $ZnSO_4 \cdot 7H_2O$ was added dropwise to the above mixture for 70 minutes and as a result, the mixture was clouded (pH: about 11). The cloudy liquid was adjusted to pH 9.5 by adding 5 mL of concentrated hydrochloric acid thereto and stirred continuously for further 4 hours. The reaction liquid was filtered using a No. 2 filter paper and the resulting solid was returned to the 200 mL beaker containing 100 mL of water, which was then washed with water by decantation. The solid obtained from the cloudy liquid by filtration using a No. 2 filter paper was dried at 50° C. for 5 hours and pulverized to obtain 8.3 g of a white powder.

The amount of sodium pyrithione recovered from the filtrate and the solution used for washing was 0.03 g as iron pyrithione.

The resulting white powder was subjected to X-ray diffraction analysis, with the result that a diffraction pattern showing the presence of zinc pyrithione and zinc oxide was obtained.

Example 2

Synthesis of a Compound (2)

In the above Example 1, the clouded liquid was stirred further for one hour after adjusted to pH 9.5 instead of carrying out a stirring operation for 4 hours and then the reaction liquid was raised to 90 to 100° C., followed by stirring for one hour. The washing with water was repeated three times. Other than the above operations, the same procedures were carried out using the same raw materials that were used in Example 1 in the same manner as in Example 1 to obtain 7.4 g of a white powder.

The amount of sodium pyrithione recovered from the filtrate and the solution used for washing was 0.13 g as iron pyrithione.

The resulting white powder was subjected to X-ray diffraction analysis, with the result that the chart showed a similar pattern to that obtained in Example 1.

Example 3

Synthesis of a Compound (3)

1000 mL of an aqueous solution containing 260.4 g (1.75 mol) of sodium pyrithione and 1800 mL of an aqueous solution containing 152 g (3.8 mol) of sodium hydroxide were combined and placed in a 10 L glass reactor, which was then kept at 20° C. 4000 mL of an aqueous solution containing 506 g (1.75 mol) of zinc sulfate $ZnSO_4.7H_2O$ was added dropwise to the above mixture for 100 minutes to cause the solution to be cloudy (pH: about 11). About 180 mL of concentrated hydrochloric acid was added dropwise to this liquid to adjust the pH to 9.5. Then, the liquid was kept at about 20° C. and stirred continuously for about 4 hours. The reaction liquid was subjected to filtration using a No. 2 filter paper and the obtained solid was returned to the 10 L reactor containing 2000 mL of purified water and washed with water by decantation. This water washing was repeated twice, to confirm that the filtrate was not colored in a violet color by iron (II) ions. Then, the solid obtained by the filtration using a No. 2 filter paper was dried at 50° C. for 5 hours and pulverized to obtain 344.2 g of a white powder. The melting point of the solid was 250° C. or higher.

The resulting white powder was subjected to X-ray diffraction analysis and, as a result, the chart showed a similar pattern to those obtained in Examples 1 and 2. Also, the infrared absorption spectrum (IR) showed the same pattern as that of zinc pyrithione.

Next, in order to separate the zinc pyrithione-zinc oxide complex compound from zinc oxide obtained as the byproduct, 400 mg of the obtained white powder was added to 300 mL of chloroform placed in a 500 mL conical flask and the mixture was stirred at 60° C. for 60 minutes. The mixture was subjected to filtration using a membrane filter under reduced pressure and the filtrate was subjected to a Soxhlet's extractor to distill chloroform in the solution on a boiled water bath. The distillation residue was dried at 60° C. for 4 hours to obtain about 340 mg of a zinc pyrithione-zinc oxide complex compound. The melting point of this compound was 241 to 245° C. This operation was further repeated twice to obtain zinc pyrithione-zinc oxide complex compounds in amounts of about 340 mg and about 330 mg. Taking it into account that the molar ratio of the sodium pyrithione and zinc sulfate used was 1:1 and that a small amount of unreacted sodium pyrithione was included (yield of a white powder: 94 W %), the chemical structure of the zinc pyrithione-zinc oxide complex compound was estimated to be $(Py)_2Zn.1/3ZnO$ (where Py represents a pyrithione anion). As a result of the X-ray diffraction analysis of this compound, the peak corresponding to zinc oxide disappeared from the chart. It is inferred that the zinc oxide part constituting the complex compound is amorphous.

The white powder and chloroform extract in this example were subjected to fluorescent X-ray analysis to compare the both with each other in respect to the ratio of zinc to other elements, thereby finding the relative content of zinc, with the result that the both had the following compositions: white powder: zinc: 72.35% and other elements: 26.5%, chloroform extract: zinc: 64.25% and other elements: 35.75%, showing that when the amount of zinc in the white powder was 1, the amount of zinc in the chloroform extract was 0.69. This value was very close to the theoretical value 0.67 and therefore this fact proves that the ratio by equivalent of zinc in the above zinc pyrithione to zinc in the above zinc oxide is 1:1/3. Also, when the elemental analysis of each element C, H, and O in the chloroform extract was made, the following results were obtained.

Measured value (%): C: 35.21, H: 2.76, O: 11.56
Calculated value (%): C: 34.80, H: 2.34, O: 10.84

It was confirmed from the above data that the chemical structure of the chloroform extract was $(Py)_2Zn.1/3ZnO$ as was estimated.

Also, the results of each thermal analysis (TG/DTA) of the obtained white powder and chloroform extract showed that the endothermic peak temperature and exothermic peak temperature of the former compound were about 268° C. and about 332° C. respectively and the endothermic peak temperature and exothermic peak temperature of the latter compound were about 265° C. and about 310° C. respectively. Moreover, with regard to the mixture obtained by powder-mixing zinc pyrithione with zinc oxide in a ratio by weight of 3:1 and zinc pyrithione, the endothermic peak temperatures of the former compound and the latter compound were about 265° C. and about 263° C. and the exothermic peak temperatures of the former compound and the latter compound were about 314° C. and about 311° C. The clear difference in data between the white powder and other three materials suggests the possibility that in the obtained white powder, the zinc pyrithione-zinc oxide complex compounds are associated among them or the complex compound is associated with zinc oxide produced as a byproduct.

Example 4

Synthesis of a Compound (4)

1000 mL of an aqueous solution containing 248.6 g (1.67 mol) of sodium pyrithione and 800 mL of an aqueous solution containing 70 g (1.75 mol) of sodium hydroxide were combined and placed in a 10 L glass reactor, which was then kept at 20° C. 2800 mL of an aqueous solution containing 483 g (1.67 mol) of zinc sulfate $ZnSO_4.7H_2O$ was added dropwise to the above mixture for 100 minutes to cause the solution to be cloudy (pH: about 10). About 5 mL of concentrated hydrochloric acid was added to this cloudy liquid to adjust the pH to 9.5. Then, the liquid was kept at 20° C. and stirred continuously for about 4 hours. The reaction liquid was subjected to filtration using a No. 2 filter paper and the obtained solid was returned to the 10 L reactor containing 2000 mL of purified water and washed with water by decantation. This water washing was repeated twice, to confirm that the filtrate was not colored in a violet color by iron (II) ions. Then, the solid obtained by the filtration using a No. 2 filter paper was dried at 50° C. for 5 hours and pulverized to obtain 335.2 g of a white powder.

The resulting white powder was subjected to X-ray diffraction analysis and, as a result, the chart showed the same pattern as those obtained in Examples 1, 2 and 3.

Example 5

Synthesis of a Compound (5)

The molar ratios of zinc sulfate and sodium hydroxide to sodium pyrithione were altered to 1:3/4 and 1:3/2 from 1:1 and 1:2 or little more used in Examples 1 to 4 respectively to make the test. 50 mL of an aqueous sodium pyrithione solution obtained by adding purified water to 32.3 g (0.087 mol) of an aqueous 40 w % sodium pyrithione solution (Trade name: "Tomicide S" manufactured by API Corporation) and 90 mL of an aqueous solution containing 5.2 g (0.13 mol) of sodium hydroxide were combined with each other and placed in a 500 mL conical flask, which was then kept at 20° C. 200 mL of an aqueous solution containing 18.8 g (0.065 mol) of zinc sulfate $ZnSO_4.7H_2O$ was added dropwise to the above mixture for 60 minutes and as a result, the mixture was cloudy (pH: about 11). About 8 mL of concentrated hydrochloric acid was added dropwise to this liquid to adjust the pH to 9.5. Then, the liquid was kept at about 20° C. and stirred continuously for about 4 hours. The reaction liquid was subjected to filtration using a No. 2 filter paper and the obtained solid was returned to the 200 mL beaker containing 100 mL of purified water and washed with water by decantation. This water washing was repeated once, to confirm that the filtrate was not colored by iron (II) ions. Then, the solid obtained by the filtration was dried at 50° C. for 5 hours and pulverized to obtain 15.0 g of a white powder.

The resulting white powder was subjected to X-ray diffraction analysis and, as a result, the chart showed the presence of zinc pyrithione and zinc oxide in the same manner as in Examples 1 to 4. When the chart of this example was compared with the chart of Example 3, the intensity ratio of the angle of diffraction specific to zinc pyrithione at 2θ=about 25° to the angle of diffraction specific to zinc oxide at 2θ=about 360 was measured, which permitted of such inference that the white powder comprised an effective component containing zinc pyrithione and a zinc pyrithione/zinc oxide complex compound in a ratio of 7:3 and zinc oxide or comprised a complex compound in which zinc pyrithione was combined with zinc oxide in a ratio 1:1/10 and zinc oxide. Also, the obtained white powder was extracted with chloroform in the same manner as in Example 3 and as a result, about 350 mg of an extract was obtained from 400 mg of the white powder. It was almost inferred from this result and also from the above ratios of raw materials and the yield of the white powder that the extract was a mixture of zinc pyrithione and a zinc pyrithione/zinc oxide complex in a ratio of 7:3 or a complex compound in which zinc pyrithione was combined with zinc oxide in a ratio 1:1/10.

Example 6

Synthesis of a Compound (6)

19.7 g of a white powder was obtained in the same manner as in Example 5 except that the amounts of zinc sulfate and sodium hydroxide were altered to 1.3 mol and 0.26 mol which were twice the amounts used in Example 5 from 0.065 mol and 0.13 mol respectively. The pH value during reaction was about 11. The resulting white powder was extracted with chloroform in the same manner as in Example 3 and as a result, about 260 mg of a zinc pyrithione/zinc oxide complex compound was obtained from 400 mg of the white powder. Taking it into account that the molar ratio of the sodium pyrithione and zinc sulfate used was 1:3/2 and that unreacted sodium pyrithione was included (yield of a white powder: 90 W %) in a considerably higher amount than in Example 3, the chemical structure of the zinc pyrithione/zinc oxide complex compound was estimated to be $(Py)_2Zn.1/3ZnO$ like that of Example 3.

Comparative Example 1

Synthesis of a Compound (7)

The same procedures as in Example 1 were conducted except that the molar ratio of zinc sulfate to sodium pyrithione was altered to 1:1/2 from 1:1 used in Examples 1 to 3 and the number of washings with water was altered to 2, to obtain a white powder (pH value: about 11).

The amount of sodium pyrithione to be used was 0.0415 mol, the amount of zinc sulfate to be used was 0.0208 mol, the amount of the obtained white powder was 6.2 g and the amount of the pyrithione recovered from the filtrate and the water washing solution was 0.09 g as iron pyrithione.

The obtained white powder was subjected to X-ray analysis and as a result, the chart showed the same pattern as that of zinc pyrithione (reagent manufactured by Wako Pure Chemical Industries, Ltd.).

Also, the results of each thermal analysis (TG/DTA) of the obtained white powder showed that the endothermic peak temperature and exothermic peak temperature of the white powder were about 268° C. and about 326° C. respectively whereas the endothermic peak temperature and exothermic peak temperature of zinc pyrithione (reagent manufactured by Wako Pure Chemical Industries, Ltd.) were about 262° C. and about 311° C. respectively. This difference suggests the possibility that the zinc pyrithione/zinc oxide complex compound produced partly is associated with zinc pyrithione through zinc oxide.

Comparative Example 2

Synthesis of a Compound (8)

The same procedures as in Example 1 were conducted except that the molar ratio of zinc sulfate to sodium pyrithione was altered to 1:2 from 1:1 used in Examples 1 to 3 and the number of washings with water was altered to 2, to obtain a white powder. The melting point of the white powder was 235 to 238° C.

The amount of sodium pyrithione to be used was 0.0415 mol, the amount of zinc sulfate to be used was 0.0830 mol, the amount of the obtained white powder was 11.8 g and the amount of the pyrithione recovered from the filtrate and the water washing solution was 0.04 g as iron pyrithione. The pH value after zinc sulfate was added dropwise to the aqueous mixed solution of sodium pyrithione and sodium hydroxide was about 7. From the results of the yield of the white powder and X-ray diffraction analysis, it was predicted that the white powder was a mixture or a complex compound of zinc pyrithione and zinc oxide monohydrate (zinc hydroxide). Moreover, 400 mg of the white powder was dissolved in 300 mL of chloroform, which was filtered and the filtrate was subjected to distillation and extraction to obtain a chloroform soluble component in an amount of 190 mg. In consideration of the relation (1:3) of the equivalents of zinc pyrithione and zinc oxide-monohydrate and the presence of a small amount of unreacted sodium pyrithione, it was inferred that the product was a mixture of zinc pyrithione and zinc oxide-monohydrate. Specifically, it is not considered that a zinc pyrithione complex compound is not produced in the reaction condition of pH 7.

Example 7

Synthesis of a Compound (9)

6.9 g of a dark green powder was obtained in the same condition and manner as in Example 2 except that zinc sulfate $ZnSO_4.7H_2O$ was replaced with $CuSO_4.5H_2O$ in an equal mol. This powder had an appearance different from that of a bright green copper pyrithione.

Example 8

Synthesis of a Compound (10)

50 mL of an aqueous sodium pyrithione solution obtained by adding 32.5 g (0.087 mol) of an aqueous 40 w % sodium pyrithione solution (Trade name: "Tomicide S" manufactured by API Corporation) to purified water and 90 mL of an aqueous solution containing 7.6 g of sodium hydroxide were combined with each other and placed in a 500 mL conical flask, which was then kept at 20° C. 200 mL of an aqueous solution containing 21.7 g (0.087 mol) of copper sulfate $CuSO_4.5H_2O$ was added dropwise to the above mixture for 60 minutes and as a result, the mixture became cloudy with a dark green color (pH: about 11). About 8.5 mL of concentrated hydrochloric acid was added to this cloudy liquid to adjust the pH to 9.5. Then, the liquid was kept at about 20° C. and stirred continuously for about 4 hours. The reaction liquid was subjected to filtration using a No. 2 filter paper and the obtained solid was returned to the 500 mL beaker containing 200 mL of purified water and washed with water by decantation. This water washing was repeated once, to confirm that the filtrate was not colored by iron (II) ions. Then, the solid obtained by the filtration was further washed with 50 mL of purified water, dried at 50° C. for 5 hours and pulverized to obtain 17.9 g of a dark green powder.

The resulting dark green powder was subjected to X-ray diffraction analysis. As a result, the dark green powder had poorly crystallized and a peak of diffraction angle of copper (II) hydroxide besides that of copper pyrithione, though it was indistinct, was observed. Also, the infrared absorption spectrum (IR) of the dark green powder showed the same pattern as that of copper pyrithione. In order to separate the copper pyrithione complex compound from copper (II) hydroxide, 400 mg of a dark green powder was weighed and extracted with chloroform in the same method as in Example 3 to obtain about 330 mg of a dark green chloroform extract. This powder had an appearance different from that of a bright green copper pyrithione.

As a result of X-ray diffraction analysis of the chloroform extract, the same diffraction angle peak as that of copper pyrithione was observed though there were a difference in peak intensity between the both. Also, as a result of thermal analysis (TG/DTA), the exothermic peak temperature was about 285° C. and the endothermic peak showing the presence of water of crystallization was observed at about 180° C. In the case of the above dark green powder, on the other hand, the exothermic peak temperature was about 282° C. and the endothermic peak showing the presence of water of crystallization was observed at about 176° C. As to the chemical components of a chloroform extract, the chloroform extract was estimated to be a copper pyrithione/copper (II) hydroxide complex compound or a mixture of a copper pyrithione/copper (II) hydroxide and a copper pyrithione/copper (II) oxide complex compound. A copper (II) hydroxide or copper (II) oxide component of the copper pyrithione complex compound is considered to be amorphous.

Example 9

Synthesis of a Compound (11)

17.5 g of a dark green powder was obtained by carrying out synthesis in the same manner as in Example 8 except that 14.8 g (0.087 mol) of copper (II) chloride $CuCl_2.2H_2O$ was used in place of copper (II) sulfate, the amount of sodium hydroxide to be used was altered to 3.8 g (0.087 mol) from 7.6 g (0.174 mol) and the stirring temperature after the aqueous copper chloride solution was added dropwise was altered to 60° C. from 20° C. The pH value after the aqueous copper chloride solution was added dropwise was about 10.

The resulting dark green powder was subjected to X-ray diffraction analysis and, as a result, the diffraction angle peaks corresponding to copper pyrithione and copper (II) oxide were observed in the chart. Also, the infrared absorption spectrum (IR) showed the same pattern as that of copper pyrithione.

Next, in order to separate the copper pyrithione/copper (II) oxide complex compound from copper (II) oxide obtained as the byproduct, 400 mg of the obtained dark green powder was weighed to carry out extraction with chloroform in the same manner as in Example 3 to obtain about 350 mg of a dark green chloroform extract, namely, a copper pyrithione/copper (II) oxide complex compound. This operation was repeated twice to obtain copper pyrithione/copper (II) oxide complex compounds in amounts of about 350 mg and about 340 mg. The copper pyrithione/copper (II) oxide complex compound was estimated to have a chemical structure $(Py)_2Cu.1/3CuO$ by the estimating method of Example 3. As a result of the X-ray diffraction analysis of this compound, the chart showed the same diffraction angle peaks as those of the chloroform extract and copper pyrithione (manufactured by API Corporation): however, the intensities of the diffraction angle were different from each other. Also, the peak corresponding to copper (II) oxide disappeared from the X-ray diffraction chart of the above dark green powder. It is inferred that like that of Example 3, the copper (II) oxide part constituting the complex compound is amorphous. The dark green powder and the chloroform extract in this example were subjected to fluorescent X-ray analysis to compare the both with each other with respect to the relative ratio of copper of the both in the same manner as in Example 3, thereby finding that the relative content of copper was 0.65 (dark green powder: copper: 74.10% and other elements: 25.90%, chloroform extract: copper: 65.04% and other elements: 34.96%). The ratio by equivalent of copper in the above copper pyrithione to copper in the above copper (II) oxide is 1:1/3. Also, when the elemental analysis of each element C, H, and O in the chloroform extract was made, the following result was obtained.

Measured value (%): C: 35.83, H: 2.74, O: 11.62

Calculated value (%): C: 35.08, H: 2.35, O: 10.90

It was confirmed from the above data that the chemical structure of the chloroform extract was $(Py)_2Cu.1/3CuO$ (II) as was estimated. The melting point of this chloroform extract was 247° C. (decomposed). Also, the results of each thermal analysis (TG/DTA) of the chloroform extract, namely, the copper pyrithione/copper (II) oxide complex compound showed that the exothermic peak temperature was about 293° C. and the endothermic peak showing the presence of water of crystallization was not observed. It is to be noted that the exothermic peak temperature of the above dark green powder was about 290° C. and the exothermic peak temperature of copper pyrithione (manufactured by API Corporation) was about 299° C.

Example 10

Synthesis of a Compound (12)

15.1 g of a dark green powder was obtained (pH: about 11, yield of the dark green powder: 98 W %) by carrying out the same procedures as in Example 9 except that the amount of copper (II) chloride was altered to 0.065 mol from 0.087 mol and the amount of sodium hydroxide was altered to 0.13 mol from 0.087 mol. The resulting dark green powder was subjected to X-ray diffraction analysis and, as a result, the chart showed the presence of copper pyrithione and copper (II) oxide in the same manner as in Example 9. When the chart of this example was compared with the chart of Example 9, the intensity ratio of the angle of diffraction specific to copper pyrithione at 2θ=about 28° to the angle of diffraction specific to copper (II) oxide at 2θ=about 35° was measured, which permitted of such inference that the dark green powder almost comprised an effective component containing copper pyrithione and a copper pyrithione/copper oxide complex compound in a ratio of 1:1 and copper (II) oxide or comprised a complex compound in which copper pyrithione was combined with copper oxide in a ratio 1:1/6 and copper (II) oxide.

Example 11

Synthesis of a Compound (13)

9.6 g of an aqueous solution (solution (trade name: "Tomicide S" manufactured by API Corporation) containing about 40 W % of sodium pyrithione and 6.4 g of sodium hydroxide (purity: 96 W %)/490 mL of water were placed in a 1000 mL flask to prepare a total 500 mL of an aqueous mixed solution, whose temperature was controlled to 20° C. 150 mL of an aqueous mixed solution in which 14.4 g of zinc sulfate heptahydrate and 6.1 g of aluminum chloride hexahydrate was dissolved in water was separately produced, and added dropwise to the above aqueous mixed solution of sodium pyrithione and sodium hydroxide over one hour to react the mixture (clouded). Moreover, 100 mL of water was added to the reaction liquid to adjust the pH to 9.5. After the liquid was stirred at 20° C. for 1 hour, it was treated at 90 to 100° C. under heating for 24 hours to age the liquid. The resulting liquid was subjected to solid-liquid separation using a No. 2 filter paper and a membrane filter and water return washing was carried out using 100 mL of water twice until the filter paper was not colored by the generation of iron pyrithione even if 0.5 g iron (II) sulfate heptahydrate/20 mL aqueous solution was added. Then, solid-liquid separation was carried out again, and the solid was dried and then pulverized to obtain 7.8 g of white microcrystals that were slightly bluish which was specific to hydrotalcite. From the results of X-ray analysis and thermal analysis (TG/TDA) and from the fact that a DMSO soluble material was not colored in brown that was a color specific to zinc pyrithione, the major components of the crystals were estimated to be a mixture of $3Zn(OH)_2 \cdot 2Al(OH)_3 \cdot Zn(Py)_2 \cdot 3H_2O$ or $Zn_4Al_2(OH)_{12}(Py)_2 \cdot 3H_2O$, a zinc pyrithione/zinc oxide complex compound and zinc oxide. As all the waters, purified water was used.

Example 12

Synthesis of a Compound (14)

(i) 415 mL of an aqueous 1 mol/L sodium pyrithione solution and 1300 mL of an aqueous 2 mol/L sodium hydroxide solution were placed in a 5 L flask and mixed, and the resulting mixture was kept at 20° C. 1200 mL of an aqueous mixed solution prepared by adding water to 239 g of zinc sulfate heptahydrate $ZnSO_4 \cdot 7H_2O$ and 100 g of aluminum chloride hexahydrate $AlCl_3 \cdot 6H_2O$ was added dropwise to the above mixture over 90 minutes, which was then adjusted to pH 9.5 by using concentrated hydrochloric acid, followed by stirring for one hour. The mixed liquid was further stirred at 90 to 100° C. for 24 hours and then cooled. The reaction liquid was filtered and the obtained cake-like solid was washed with 100 mL of water. Then, water return washing was carried out using 1000 mL of water four times and the solid separated by filtration was dried at 50° C. for 5 hours, followed by pulverized to obtain 147.3 g of a slightly bluish white powder. From the results of X-ray analysis, thermal analysis (TG/TDA) and a DMSO dissolution test, the major components of the powder were estimated to be a mixture of $3Zn(OH)_2 \cdot 2Al(OH)_3 \cdot Zn(Py)_2 \cdot 3H_2O$ or $Zn_4Al_2(OH)_{12}(Py)_2 \cdot 3H_2O$, a zinc pyrithione/zinc oxide complex compound and zinc oxide. As all the waters, purified water was used.

(ii) 15 W % of 415 mL of the aqueous 1 mol/L sodium pyrithione solution was replaced with an aqueous 0.5 mol/L sodium carbonate $Na_2CO_3$ (anhydride) solution.

The amount of the wet cake obtained in this manner was 670 g. Among 670 g of the wet cake, 190 g of the wet cake was weighed and was treated in the same manner as in this example (i). As a result, 46 g of slightly bluish white microparticle crystals was obtained. From the results of X-ray analysis and thermal analysis (TG/TDA), the major components of the crystals were estimated to be a mixture of $3Zn(OH)_2 \cdot 2Al(OH)_2 \cdot Zn(Py)_{1.6}(CO_3)_{0.2} \cdot 3H_2O$ or $Zn_4Al_2(OH)_{12}(Py)_{1.6}(CO_3)_{0.2} \cdot 3H_2O$ and a zinc pyrithione/zinc oxide complex compound. In this case, the diffraction angle peaks peculiar to carbonic acid type hydrotalcite and zinc pyrithione were observed. However, though zinc oxide was not present, no coloring by iron (II) ions was observed and also no coloring was observed in the DMSO dissolution test of Example 11. It was therefore inferred that zinc pyrithione was not present and the diffraction angle peak of zinc pyrithione was estimated to be derived from a complex compound of zinc pyrithione and zinc oxide. As all the waters, purified water was used.

Example 13

Stability in DMSO

Each stability of the compounds of Examples 3, 4 and 12(i) and zinc pyrithione in dimethylsulfoxide (DMSO) was investigated. 2 g of each of these four compounds was added in 10 g of DMSO, allowed to stand at ambient temperature in a laboratory and filtered, to examine coloring of the filtrate. Then, the filter residue was again added to 10 g of DMSO to carry out the same operation. As a result, in the case of zinc pyrithione, both the first and second filtrates exhibited a brown appearance whereas in the case of the compounds of Examples 3 and 4, slight yellowing was observed in the first filtrate but no coloring was observed in the second filtrate. In the case of the compound of Example 12(i), no coloring was observed at all in both the first and second filtrates. Further, the above filtrates were placed in the laboratory for 6 months to observe the state of the appearance with no consequent change. This shows that the pyrithione complex compound of the present invention is stable in a polar solvent such as DMSO and, at the same time, the complex compound is not easily decomposed into zinc pyrithione.

Example 14

Antibacterial Activity (1)

The white powder obtained in the above Example 4 was subjected to an antibacterial test (MIC) to compare with zinc pyrithione. The results are shown in Table 1.

Preparation of a sample: the white powder is added in a fixed concentration.

Test strains: *Escherichia coli* IFO 3972
*Bacillus subtilis* IFO 3215
Culture condition: 28° C., 24 hours, shake culture

TABLE 1

Minimum growth inhibitive concentration of bacteria (mg/L)

|  | *Escherichia coli* | *Bacillus subtilis* |
|---|---|---|
| Example 4 White powder | 2.5 | 2.5 |
| Control: Zinc pyrithione | 5 | 2.5 |

Example 15

Antibacterial Activity (2)

The white powder obtained in the above Example 12(i) was subjected to an antibacterial test (MIC) to compare with zinc pyrithione. The results are shown in Table 2. The preparation of a sample, test strains and culture condition are the same as those of Example 14.

TABLE 2

Minimum growth inhibitive concentration of bacteria (mg/L)

|  | *Escherichia coli* | *Bacillus subtilis* |
|---|---|---|
| Example 12(i) White powder | 5 | 5 |
| Control: Zinc pyrithione | 2.5 | 1 |

Example 16

Antibacterial Activity (3)

The white powder obtained in the above Example 4 was subjected to an antibacterial test (MIC) to compare with zinc pyrithione and an isothiazolone type aqueous preparation (Keison WT) and to an antibacterial test (MIC) in the case of combining the sample with the above isothiazolone type aqueous preparation.

The results are shown in Table 3. The preparation of a sample, test strains and culture condition are the same as those of Example 14.

Test strains: *Pseudomonas aeruginosa* IAM 1514

TABLE 3

Minimum growth inhibitive concentration of bacteria (mg/L)

|  | *Pseudomonas aeruginosa* |
|---|---|
| Example 4 White powder | 500 |
| Control: Zinc pyrithione | >1000 |

TABLE 3-continued

Minimum growth inhibitive concentration of bacteria (mg/L)

|  | *Pseudomonas aeruginosa* |
|---|---|
| Control: Isothiazolone aqueous preparation (Kathon WT) | 25 |
| White powder of Example 4 + isothiazolone aqueous preparation (Kathon WT) (1:1) | 25 |

Note:
Kathon WT: An aqueous 14% solution by formulating, as active ingredients, 5-chloro-2-methyl-3-isothiazolone and 2-methyl-3-isothiazolone in a ratio by weight of 3:1.

Example 17

Antibacterial Activity (4)

The chloroform extract obtained in Example 3 was subjected to an antibacterial test (MIC) to compare with zinc pyrithione. The results are shown in Table 4.

Preparation of a sample: the extract was dissolved in dimethylsulfoxide, to which an aqueous 0.1 W % Tween 80 was added to make a sample solution.

Type of test strains and conditions of culture medium and culture

1. *Escherichia coli* NBRC 3972

NB agar medium to which lactose is added, 30° C., 3 days

2. *Malassezia furfur* NBRC 0656

YM agar medium to which olive oil is added, 30° C., 6 days

3. *Staphylococcus aureus* NBRC 12732

Soybean casein digest agar medium, 30° C., 5 days

TABLE 4

Minimum growth inhibitive concentration of bacteria (mg/L)

|  | *Escherichia coli* | *Malassezia furfur* | *Staphylococcus aureus* |
|---|---|---|---|
| Example 3 Chloroform extract | 10 | 5 | 1.25 |
| Control: Zinc pyrithione | 20 | 5 | 2.5 |

Example 18

Antibacterial Activity (5)

The chloroform extract obtained in the above Example 9 was subjected to an antibacterial test (MIC) to compare with copper pyrithione (API Corporation). The results are shown in Table 5.

Preparation of a sample: same as in Example 17

Type of test strains and conditions of culture medium and culture

*Aspergillus niger* ATCC 6275

Potato dextrose agar medium, 30° C., 7 days

TABLE 5

Minimum growth inhibitive concentration of bacteria (mg/L)

|  | Aspergillus niger |
|---|---|
| Example 9 Chloroform extract | 5 |
| Control: Copper pyrithione | 20 |

Example 19

Algicidal Activity (1)

Each white powder obtained in the above Examples 2 and 11 was subjected to a test as to algicidal activity. The sample was heated under reduced pressure at 150° C. for 10 minutes. The sample was added in amounts of 0.1 mg, 1 mg and 10 mg respectively to 100 mL of sterilized artificial seawater (salt concentration: 3.5 W %, pH 8.3) so as to adjust concentrations of 1 mg/L, 10 mg/L and 100 mg/L. Sea lettuce which was sampled the day before the test at Yuasa coast in Wakayama prefecture and stored in a refrigerator while it was dipped in seawater was cut into small species of 2 cm×2 cm, which were washed with artificial seawater. Then, three sample species were added in each test solution, which was stirred (60 r.p.m.) under illumination at ambient temperature for 24 hours, to observe a change in the color of the sea lettuce. As a result, the concentration of each sample of the white powders of both Examples 2 and 11 at which a part of the sea lettuces was changed in color from bright green to dark green was 1 mg/L and the concentration at which all these three pieces were changed in color to dark green was 10 mg/L. When the sea lettuces changed in color to dark green were observed by an optical microscope, destruction of cells was observed. In the case of the sea lettuces which were subjected to the same test using seawater to which the sample was not added, no color change was observed.

Example 20

Solubility in Artificial Seawater

With regard to the chloroform extracts of Examples 3 and 9, zinc pyrithione (reagent manufactured by Wako Pure Chemical Industries Ltd.) and copper pyrithione (API Corporation), zinc and copper dissolved in artificial sea water having the following formulation were measured by atomic absorption analysis to convert the measured data into molecular weight, thereby measuring the solubility in artificial seawater. The results are shown in Table 6.

Formulation of artificial seawater (g/L)

| | |
|---|---|
| NaCl | 24.53 |
| $MgCl_2 \cdot 6H_2O$ | 11.11 |
| $Na_2SO_4$ | 4.09 |
| $CaCl_2$ | 1.54 |
| KCl | 0.695 |
| $NaHCO_3$ | 0.201 |
| KBr | 0.100 |
| $H_3BO_3$ | 0.027 |
| $SrCl_2 \cdot 6H_2O$ | 0.042 |
| NaF | 0.003 |

Method of Measurement 0.1 g of the sample was added in 500 mL of artificial seawater, which was then stirred at 20° C. and 30° C. for 4 hours and filtered, and the filtrate was subjected to atomic absorption analysis.

TABLE 6

Solubility in seawater (mg/L), pH = 8.2

| | 20° C. | | 30° C. | |
|---|---|---|---|---|
| | Dissolved zinc-copper | Molecular weight conversion | Dissolved zinc-copper | Molecular weight conversion |
| Example 3 Chloroform extract | 0.82 (Zn) | 3.2 | 1.09 (Zn) | 4.3 |
| Example 9 Chloroform extract | 0.14 (Cu) | 0.6 | 0.15 (Cu) | 0.6 |
| Control: zinc pyrithione | 1.26 (Zn) | 6.1 | 1.52 (Zn) | 7.4 |
| Control: copper pyrithione | 0.02 (Cu) | 0.1 | 0.05 (Cu) | 0.2 |

Example 21

Liquid Shampoo

Each component in the following composition was mixed homogeneously to obtain a liquid shampoo.

| | |
|---|---|
| Sodium polyoxyethylene (EO = 2 mol) lauryl ether sulfate | 16.0 W % |
| Coconut oil fatty acid diethanolamide | 6.0 W % |
| Hydroxyethyl cellulose | 0.3 W % |
| White powder of Example 4 | 1.5 W % |
| Citric acid | small amount |
| Purified water | Balance |
| Total | 100.0 W % (pH = 6.0) |

Example 22

Antifouling Paint for Ship Bottom

Each component in the following composition was homogeneously mixed by using a propeller crusher to obtain an antifouling paint for ship bottom.

| | |
|---|---|
| Vinyl chloride/isobutyl vinyl ether copolymer (50 W % xylene solution) | 10.0 W % |
| Cuprous oxide | 20.0 W % |
| Iron oxide red | 8.0 W % |
| White powder of Example 3 | 3.0 W % |
| Talc | 12.0 W % |
| Rosin (60 W % xylene solution) | 25.0 W % |
| Fatty acid polyamide wax (20 W % xylene solution) | 2.0 W % |
| Xylene | 10.0 W % |
| Solvesso 100 (ESSO) | 10.0 W % |
| Total | 100.0 W % |

A change in the viscosity (or gelation) of the paint was not observed during the course of preparation of this antifouling paint for ship bottom and in investigation made by opening a can containing the paint. Also, an anticorrosive-treated steel sheet panel (10 cm×30 cm) was coated with the paint prepared in this manner such that the coating thickness was 120 μm and the resulting panel was soaked in a hanging state in seawater of Aioi bay in Hyogo prefecture since the end of November, 2002 until the end of August, 2003. It was not observed that fouling organisms were stuck to the panel coated with the antifouling paint of the present invention nine months after the panel was soaked. On the other hand, it was observed that sea lettuces were stuck to the panel coated with the paint in which talc was additionally formulated in place of the white powder of Example 3 having the above composition.

Example 23

Antifouling Agent for Fish-Farming Nets

Each component in the following compositions was homogeneously mixed to obtain two (formulation I and formulation II) antifouling agents for fish-farming net.

| | |
|---|---|
| Butylacrylate-methylmethacrylate copolymer (50 W % xylene solution) | 20.0 W % |
| Cuprous oxide | 15.0 W % |
| White powder (formulation I) of Example 3 or Dark green powder (formula II) of Example 9 | 2.0 W % |
| Polyether silicon oil | 2.0 W % |
| Disparon 4200-20 (Kusumoto Kasei (k.k.)) | 3.0 W % |
| Xylene | 58.0 W % |
| Total | 100.0 W % |

A polyethylene fish-farming net (6 knots, 400 deniers, 60 strings) was dipped in the fish-farming net antifouling agent having the above formulation to coat the net with antifouling agent, which was then dried in air. This net was soaked in seawater of Aioi bay in Hyogo prefecture since the end of May, 2003 until the end of August, 2003. It was not observed that fouling organisms were stuck to the net treated with the agents having the formulations (I) or (II). On the other hand, it was observed that a large amount of sea lettuces were stuck to the net treated with the agent which contained neither the white powder of Example 3 nor the dark green powder of Example 9 and additionally formulated of talc instead. The preserving stability of each antifouling agent for fish-farming nets having the above formulations I and II respectively was good.

Example 24

Antibacterial Preparation

Each component in the following composition was homogeneously mixed to obtain an antibacterial preparation.

| | |
|---|---|
| White powder of Example 4 | 10.0 W % |
| Demol N (aromatic anionic dispersant, Kao Corporation) | 0.5 W % |
| Carboxymethyl cellulose | 0.1 W % |
| Water | Balance |
| Total | 100.0 W % |

The above antibacterial preparation was added to 10 mL of a test solution obtained by combining 0.3 mL of a slime solution which was pre-cultured at 35° C. using slimes generated in the circulating cooling water with 9.7 mL of a bouillon medium used in the above Example 14 such that the effective component (white powder of Example 4) of the preparation was 5 ppm, 10 ppm and 20 ppm and each medium was shake-cultured at 35° C. for 8 hours. The turbidity of the test solution was measured at an absorbance of 660 nm and as a result, bacterial growth inhibition was observed in an effective component concentration of 10 ppm.

Example 25

Weathering of Polyethylene Resin Molded Article

The white powder of Example 3, the chloroform extract of Example 3, the white powder of Example 12(i) and zinc pyrithione (control) were respectively added to LDPE (low-density polyethylene) having no additive in an amount of 0.15 parts based on 100 parts of the resin and the mixture was kneaded at 140° C. by using a double roll for 6 to 7 minutes. Then, the resin materials were respectively applied to a sheet having a size of 200 mm×200 mm×1.1 mm by press molding in the condition of 140° C. and 200 kgf/cm². Two test pieces of 30 mm×110 mm were cut from each of the four sheets and hung in the sun from 8 a.m. to 5 p.m. for five fine weather days selected from among the term between Sep. 15 and Sep. 25 in 2004.

Averages of a color difference (ΔE*) and YI (yellow index) between two samples, namely the sample before hung in the sun and the sample after hung in the sun are shown in Table 7.

TABLE 7

| | Sample before hung in the sun | | | | Sample after hung in the sun | | | | | |
|---|---|---|---|---|---|---|---|---|---|---|
| | L* | a* | b* | YI | L* | a* | b* | ΔE* | YI | ΔYI |
| White powder of Example 3 | 83.10 | −0.20 | 0.64 | 1.53 | 82.02 | −2.56 | 9.28 | 9.02 | 17.54 | 16.02 |
| Chloroform extract Example 3 | 84.78 | −0.28 | 0.71 | 1.58 | 81.92 | −3.05 | 11.52 | 11.52 | 21.52 | 19.93 |
| White powder of Example 12 (i) | 83.76 | −0.17 | 0.78 | 1.86 | 82.84 | −1.69 | 6.60 | 6.09 | 12.82 | 10.96 |
| Zinc pyrithione | 86.87 | −0.79 | 0.51 | 0.71 | 82.16 | −5.00 | 19.68 | 20.18 | 34.70 | 34.00 |

The degree of coloring was the smallest (not much coloring was felt visually) in the case of the white powder obtained in Example 12 (i), smaller in the case of white powder of Example 3 and the chloroform extract of Example 3 in the order named and the largest (yellow) in the case of zinc pyrithione.

Example 26

Foot Powder

Each component in the following composition was homogeneously mixed to obtain a foot powder.

| White powder of Example 4 | 3.0 W % |
| Talc | 97.0 W % |
| Total | 100.0 W % |

During the summer season in 2003, 10 tennis players were asked to spray the above antibacterial powder in their tennis shoes before they started playing tennis to examine the odor of the foot after playing tennis. As a result, all tennis players evaluated that the antibacterial powder suppressed the odor clearly.

INDUSTRIAL APPLICABILITY

The pyrithione complex compound of the present invention succeeds in imparting more excellent antibacterial and antifungal effects than a conventional pyrithione metal salt and a new hair-growing effect, and in overcoming the drawbacks to and problems on the chemical stability and qualities of a conventional pyrithione metal salt by combining a metal oxide or metal hydroxide with a conventional pyrithione metal salt.

Due to these superior characteristics, the pyrithione complex compound of the present invention may be utilized as an antidandruff/hair regrowth agent that is to be formulated in hair-care products and has a hair-regrowth effect, an antifouling agent for ship bottom paints, an antifouling agent for fish-farming nets and as an antifungal agent or a preservative/mildewcide for plastic products, rubber products, fiber products, aqueous products, wood and foot powders.

The invention claimed is:

1. A zinc pyrithione complex compound represented by the formula (I):

$$x\text{ZnO}\cdot\text{Zn}(\text{Py})_2 \qquad (I),$$

wherein x denotes a positive number satisfying the equation: $0 < x \leqq 1$, and Py represents 2-pyridylthio-N-oxide.

2. The zinc pyrithione complex compound according to claim 1, wherein x is $\frac{1}{3}$.

3. A process for producing a zinc pyrithione complex compound represented by the formula (I):

$$x\text{ZnO}\cdot\text{Zn}(\text{Py})_2 \qquad (I),$$

wherein x denotes a positive number satisfying the equation: $0 < x \leqq 1$, and Py represents 2-pyridylthio-N-oxide, said process comprising:
adding ½ to 2 equivalent mol of an aqueous solution of a water-soluble zinc salt and ¾ to 3 equivalent mol of an aqueous alkali hydroxide solution to an aqueous alkali pyrithione solution, and
reacting the mixture at a pH of 9 to 12 to collect precipitates of the zinc pyrithione complex compound represented by the formula (I).

4. The process according to claim 3, wherein x is $\frac{1}{3}$.

5. The process according to claim 3 or claim 4, wherein the zinc pyrithione complex compound contains zinc oxide or a mixture of zinc oxide and zinc pyrithione as a byproduct, and the exothermic peak temperature in thermal analysis (DTA) is 322 to 335° C.

6. An antidandruff agent comprising one or more of the zinc pyrithione complex compounds according to claim 1 or claim 2.

7. A hair-care product comprising the antidandruff agent according to claim 6.

8. A hair-care product comprising the antidandruff agent according to claim 6 and zinc oxide.

9. An underwater antifouling agent comprising one or more of the zinc pyrithione complex compounds according to claim 1 or claim 2.

10. An underwater antifouling agent comprising:
a binder,
one or more of the zinc pyrithione complex compounds according to claim 1 or claim 2, and
an inorganic copper compound and/or an inorganic zinc compound.

11. The underwater antifouling agent according to claim 10, wherein
the binder is an acrylic resin,
the inorganic copper compound is at least one type selected from the group consisting of copper (I) oxide, copper (II) oxide and copper thiocyanate, and
the inorganic zinc compound is zinc oxide.

12. A rot proofing/mildew proofing agent or antibacterial/antifungal agent comprising one or more of the zinc pyrithione complex compounds according to claim 1 or claim 2 as effective components.

13. An aqueous product comprising the zinc pyrithione complex compound according to claim 2 and a 2-isothiazolone type preservative.

14. An aqueous product comprising a mixture of the zinc pyrithione compound according to claim 2 and zinc oxide, and a 2-isothiazolone type preservative.

* * * * *